United States Patent
Cho et al.

(10) Patent No.: US 11,498,062 B2
(45) Date of Patent: Nov. 15, 2022

(54) PHOSPHORUS-CONTAINING SOLID CATALYSTS AND REACTIONS CATALYZED THEREBY, INCLUDING SYNTHESIS OF P-XYLENE

(71) Applicants: Regents of the University of Minnesota, Minneapolis, MN (US); University of Massachusetts Amherst, Amherst, MA (US); University of Delaware, Newark, DE (US)

(72) Inventors: Hong Je Cho, Amherst, MA (US); Wei Fan, Amherst, MA (US); Michael Tsapatsis, Edina, MN (US); Paul J. Dauenhauer, Shoreview, MN (US); Limin Ren, Minneapolis, MN (US); Raul Lobo, Newark, DE (US)

(73) Assignees: Regents of the University of Minnesota, Minneapolis, MN (US); University of Massachusetts Amherst, Amherst, MA (US); University of Delaware, Newark, DE (US)

( * ) Notice: Subject to any disclaimer, the term of this patent is extended or adjusted under 35 U.S.C. 154(b) by 0 days.

(21) Appl. No.: 16/337,603

(22) PCT Filed: Sep. 29, 2017

(86) PCT No.: PCT/US2017/054558
§ 371 (c)(1),
(2) Date: Mar. 28, 2019

(87) PCT Pub. No.: WO2018/064604
PCT Pub. Date: Apr. 5, 2018

(65) Prior Publication Data
US 2019/0344252 A1 Nov. 14, 2019

Related U.S. Application Data

(60) Provisional application No. 62/419,247, filed on Nov. 8, 2016, provisional application No. 62/419,202, filed
(Continued)

(51) Int. Cl.
*C07C 1/24* (2006.01)
*B01J 29/70* (2006.01)
(Continued)

(52) U.S. Cl.
CPC ............. *B01J 29/85* (2013.01); *B01J 29/40* (2013.01); *B01J 29/7007* (2013.01); *B01J 35/109* (2013.01); *B01J 35/1085* (2013.01); *B01J 37/0201* (2013.01); *B01J 37/28* (2013.01); *C07C 1/24* (2013.01); *C07C 2/865* (2013.01); *C07C 6/06* (2013.01); *C07C 51/42* (2013.01); *B01J 2229/18* (2013.01); *B01J 2229/183* (2013.01); *B01J 2229/186* (2013.01); *B01J 2229/37* (2013.01); *C07C 2521/04* (2013.01); *C07C 2521/06* (2013.01); *C07C 2521/08* (2013.01); *C07C 2521/10* (2013.01); *C07C 2521/12* (2013.01); *C07C 2521/18* (2013.01);
(Continued)

(58) Field of Classification Search
CPC . B01J 29/041; B01J 29/06; B01J 29/08; B01J 2029/081; B01J 29/40; B01J 29/7007; B01J 29/82; B01J 29/85; B01J 2229/16; B01J 2229/18; B01J 2229/183; B01J 2229/186; B01J 2229/37; B01J 35/109; B01J 35/1085; B01J 37/28; B01J 37/0201; Y02P 20/52; Y02P 20/582; C07C 2521/04; C07C 2521/06; C07C 2521/08; C07C 2521/10; C07C 2521/12; C07C 2521/18; C07C 2527/14; C07C 2527/18; C07C 2527/167; C07C 2529/08; C07C 2529/06; C07C 2529/40; C07C 2529/70; C07C 2529/82; C07C 2529/85; C07C 2/865; C07C 1/24; C07C 6/06; C07C 51/42
USPC ..... 502/60, 77, 208, 214; 585/469, 471, 475
See application file for complete search history.

(56) References Cited

U.S. PATENT DOCUMENTS 1,094,223 A 4/1914 Kyriakides
2,174,280 A 9/1939 Wellman
(Continued)

FOREIGN PATENT DOCUMENTS

EP 0307060 3/1989
RU 2153924 8/2000
(Continued)

OTHER PUBLICATIONS

Ding et al., "Combined desilication and phosphorus modification for high-silica ZSM-5 zeolite with related study of hydrocarbon cracking", Applied Catalysis A: General 503, (2015), pp. 147-155.*
(Continued)

*Primary Examiner* — Elizabeth D Wood
(74) *Attorney, Agent, or Firm* — Fish & Richardson P.C.

(57) ABSTRACT

Methods and phosphorus-containing solid catalysts for catalyzing dehydration of cyclic ethers (e.g., furans, such as 2,5-dimethylfuran) and alcohols (e.g., ethanol and isopropanol). The alcohols and cyclic ethers may be derived from biomass. One example includes a tandem Diels-Alder cycloaddition and dehydration of biomass-derived 2,5-dimethyl-furan and ethylene to renewable p-xylene. The phosphorus-containing solid catalysts are also active and selective for dehydration of alcohols to alkenes.

11 Claims, 13 Drawing Sheets

Related U.S. Application Data on Nov. 8, 2016, provisional application No. 62/414,302, filed on Oct. 28, 2016, provisional application No. 62/410,922, filed on Oct. 21, 2016, provisional application No. 62/410,919, filed on Oct. 21, 2016, provisional application No. 62/402,238, filed on Sep. 30, 2016.

(51) Int. Cl.
| | |
|---|---|
| B01J 29/85 | (2006.01) |
| B01J 29/40 | (2006.01) |
| B01J 37/28 | (2006.01) |
| C07C 2/86 | (2006.01) |
| C07C 6/06 | (2006.01) |
| C07C 51/42 | (2006.01) |
| B01J 35/10 | (2006.01) |
| B01J 37/02 | (2006.01) |

(52) U.S. Cl.
CPC ...... C07C 2523/10 (2013.01); C07C 2523/20 (2013.01); C07C 2527/167 (2013.01); C07C 2527/18 (2013.01); C07C 2527/188 (2013.01); C07C 2529/08 (2013.01); C07C 2529/40 (2013.01); C07C 2529/70 (2013.01); C07C 2529/82 (2013.01); C07C 2529/85 (2013.01)

(56) References Cited

U.S. PATENT DOCUMENTS

| | | | |
|---|---|---|---|
| 2,310,809 A | 2/1943 | Reppe et al. | |
| 3,758,612 A | 9/1973 | Maurin | |
| 3,781,222 A | 12/1973 | Weisang et al. | |
| 3,849,512 A | 11/1974 | Bowman | |
| 3,893,946 A | 7/1975 | Weisang et al. | |
| 3,957,900 A | 5/1976 | Weisang et al. | |
| 3,987,900 A | 10/1976 | Tadokoro et al. | |
| 5,457,078 A * | 10/1995 | Absil | B01J 29/7007 502/64 |
| 5,472,922 A * | 12/1995 | Degnan | B01J 29/7007 208/114 |
| 5,849,970 A | 12/1998 | Fall et al. | |
| 5,919,430 A * | 7/1999 | Hasenzahl | C07D 301/12 423/702 |
| 5,951,963 A * | 9/1999 | He | B01J 29/85 423/713 |
| 6,046,128 A * | 4/2000 | Kisen | B01J 29/40 423/239.2 |
| 6,248,924 B1 | 6/2001 | Rühl et al. | |
| 6,787,023 B1 * | 9/2004 | Mohr | B01J 29/06 208/27 |
| 8,067,214 B2 | 11/2011 | Burk et al. | |
| 8,580,543 B2 | 11/2013 | Burk et al. | |
| 8,981,172 B2 | 3/2015 | Norman | |
| 9,169,496 B2 | 10/2015 | Marliere | |
| 9,180,413 B2 | 11/2015 | Tsapatsis et al. | |
| 2003/0004383 A1 * | 1/2003 | Brown | B01J 37/0009 585/467 |
| 2010/0092383 A1 * | 4/2010 | Ying | B01J 29/084 423/718 |
| 2010/0216958 A1 | 8/2010 | Peters et al. | |
| 2013/0059722 A1 | 3/2013 | Tsapatsis et al. | |
| 2013/0066131 A1 * | 3/2013 | Harris | C07C 4/06 585/653 |
| 2013/0294991 A1 * | 11/2013 | Jones | B01J 20/327 423/228 |
| 2014/0296600 A1 * | 10/2014 | Dauenhauer | C07C 15/08 585/469 |
| 2019/0241481 A1 | 8/2019 | Delledonne | |
| 2019/0344252 A1 * | 11/2019 | Cho | C07C 51/42 |
| 2019/0345078 A1 * | 11/2019 | Abdelrahman | B01J 29/85 |

FOREIGN PATENT DOCUMENTS

| | | |
|---|---|---|
| RU | 2183499 | 6/2002 |
| WO | WO 2001/37994 | 5/2001 |
| WO | WO 2016/092063 | 6/2016 |

OTHER PUBLICATIONS

Machine Translation, JP 2011225401, Nov. 20, 2011.*
J. Ding et al., Applied Catalysis A: General 503 (2015), pp. 147-155.*
Manrique et al., "Phosphorus-Modified Beta Zeolite and Its Performance in Vacuum Fas Oil Hydrocracking Activity", Energy & Fuels, 2019, 33, pp. 3483-3491.*
Pitchumani et al., "Tuning of nanostructured SBA-15 silica using phosphoric acid", Catalysis Today, vol. 105, 3-4, 2005, pp. 618-622.*
Machin et al., "One-Dimensional (1D) Nanostructured Materials for Energy Applications", Materials, 14, 2021, pp. 1-47.*
Abdelrahman et al., "Biomass-Derived Butadiene by Dehydra-Decyclization of Tetrahydrofuran" ACS Sustain, Chem. Eng., 5:3732-6, Apr. 2017.
Camblor et al., "Spontaneous nucleation and growth of pure silica zeolite-beta free of connectivity defects," Chem. Comm., 2365-6, Jul. 1996.
Chang et al., "Lewis acid zeolites for tandem Diels-Alder cycloaddition and dehydration of biomass-derived dimethylfuran and ethylene to renewable p-xylenem," Green Chem, 18:1368-76, 2016.
Chang et al., "Rapid synthesis of Sn-Beta for the isomerization of cellulosic sugars," RSC Adv., 2(28): 10475-7, Sep. 2012.
Chang et al., "Ultra-selective cycloaddition of dimethylfuran for renewable p-xylene with H-BEA," Green Chem., 16:585-88, 2014.
Chia et al., "Selective Hydrogenolysis of Polyols and Cyclic Ethers over Bifunctional Surface Sites on Rhodium-Rhenium Catalysts" J. Am. Chem. Soc., 133:12675-89, Jul. 2011.
Cho et al., "Renewable p-Xylene from 2,5-Dinethylfuran and Ethylene Using Phosphorus-Containing Zeolite Catalysts," ChemCatChem., 9(3):398-402, Feb. 2017.
Choi et al., "Amphiphilic organosilane-directed synthesis of crystalline zeolite with tunable mesoporosity," Nat. Mater., 5: 718-23, Sep. 2006.
Choi et al., "Stable single-unit-cell nanosheets of active and long-lived catalysts," Nature, 461:246-9, Sep. 2009.
Choudhary et al.," Conversion of Xylose to Furfural Using Lewis and Brønsted Acid Catalysts in Aqueous Media," ACS Catalysis 2(9):2022-8, Aug. 2012.
Duan et al., "Efficient production of 1,3-butadiene in the catalytic dehydration of 2,3-butanediol," Applied Catalysis A: General 491:163-9, Feb. 2015.
Farneth and Gorte, "Methods for Characterizing Zeolite Acidity," Chem. Rev., 95(3):615-35, May 1995.
Freidlin and Sharf, "Two paths for the dehydration of 1,4-butanediol to divinyl with a tricalcium phosphate catalyst," Bull. Acad. Sci. USSR, Div. Chem. Sci. 9(9):1577-9, Feb. 1960.
Fyfe et al., "Detailed Investigation of the Lattice Structure of Zeolite ZSM-11 by a Combination of Solid-State NMR and Synchrotron X-ray Diffraction Techniques," J. Am. Chem. Soc., 111(7):2470-4, Mar. 1989.
Godawa et al., "Palladium catalyzed hydrogenation of furan: optimization of production conditions for tetrahydrofuran," Resources, Conservation and Recycling 3(4):201-16, Jun. 1990.
Gorte, "What do we know about the acidity of solid acids?, Catalysis Letters," 62(1):1-13, Sep. 1999.
Groen et al., "Desilication: on the controlled generation of mesoporosity in MFI zeolites," Mater. Chem., 16:2121-31, Mar. 2006.
Ichikawa et al., "Catalytic reaction of 1,3-butanediol over solid acids," J. Mol. Catal. A: Chem. 256(1-2): 106-12, Aug. 2006.
Igarashi et al., "Dehydration of butanediols over CeO2 catalysts with different particle sizes," Applied Catalysis A: General 300(1):50-7, Jan. 2006.
Jeong et al., "Oriented Molecular Sieve Membranes by Heteroepitaxial Growth," J. Am. Chem. Soc., 124(44):12966-8, Nov. 2002.

(56) References Cited

OTHER PUBLICATIONS

Jiang et al. "Biodegradation-inspired bioproduction of methylacetoin and 2-methyl-2, 3-butanediol" Sci. Rep., 3:1-7, Aug. 2013.
Jing et al., "Direct Dehydration of 1,3-butanediol into butadiene over aluminosilicate catalysts," Catal. Sci. Technol., 6(15):5830-40, Feb. 2016.
Kragten et al., "Structure of the Silica Phase Extracted from Silica/(TPA)OH Solutions Containing Nanoparticles," J. Phys. Chem. B, 107(3 7): 10006-16, Sep. 2003.
Lee et al., "Sub-40 nm Zeolite Suspensions via Disassembly of Three-Dimensionally Ordered Mesoporous-Imprinted Silicalite-1," J. Am. Chem. Soc., 133(3):493-502, Jan. 2011.
Lejemble et al., "From biomass to furan through decarbonylation of furfural under mild conditions," Biomass, 4(4):263-74, Jan. 1984.
Li et al., "Pure-Silica-Zeolite MEL Low-k Films from Nanoparticle Suspensions," J. Phys. Chem. B., 109(18):8652-8, May 2005.
Liu et al., Catalytic Behavior of Bronsted Acid Sites in MWW and MFI Zeolites with Dual Meso- and Microporosity ACS Catal., 1(1):7-17, Jan. 2011.
Maheshwari et al., "Layer Structure Preservation during Swelling, Pillaring, and Exfoliation of a Zeolite Precursor," J. Am. Chem. Soc., 130(4): 1507-16, Jan. 2008.
Makshina et al., "Review of old chemistry and new catalytic advances in the on-purpose synthesis of butadiene," Chem. Soc. Rev., 43(22), 7917-53, Mar. 2014.
Na et al., "Pillared MFI Zeolite Nanosheets of a single-Unit-Cell Thickness," J. Am. Chem. Soc., 132(12):4169-77, Mar. 2010.
Nair et al., "Zeolite-β grown epitaxially on SSZ-31 nanofibers," Chem. Commun., 10:921-2, Mar. 1999.
Pace et al., "2-Methyltetrahydrofuran (2-MeTHF): A Biomass-Derived Solvent with Broad Application in Organic Chemistry," ChemSusChem., 5(8): 1369-79, Aug. 2012.
PCT International Preliminary Report on Patentability in International Appln. No. PCT/US17/54558 dated Apr. 11, 2019, 9 pages.
PCT International Search Report and Written Opinion in International Appln. No. PCT/US17/54558 dated Jan. 26, 2018, 18 pages.
Roth et al., "MCM-36: The first pillared molecular sieve with zeolite properties," Stud. Surf. Sci. and Catal., 94:301, Jan. 1995.
Sato et al., "Dehydration of 1,4-butanediol into 3-buten-1-ol catalyzed by ceria," Catal. Comm., 5(8):397-400, Aug. 2004.
Sato et al., "Dehydration of diols catalyzed by CeO2," J. Mol. Catal. A: Chem., 221(1-2):177-83, Nov. 2004.
Sayari et al., "Simple Synthesis Route to Monodispersed SBA-15 Silica Rods," J. Am. Chem. Soc., 126(44)14348-9, Oct. 2004.
Schlenker et al., "Computed X-ray Powder Diffraction Patterns for Ultrasmall Zeolite Crystals," J. Appl. Cryst., 29(2): 178-85, Apr. 1996.
Sharf et al., "Production of isoprene from formaldehyde and isobutylene through 3-methylbutanediol-1, 3," Bull. Acad. Sci. USSR, Div. Chem. Sci., 14(9), 1621-3, Sep. 1965.
Shuikin and An, "Dehydration of tetrahydropyran over TiO2-Al2O3," Bull. Acad. Sci. USSR, Div. Chem. Sci., 9(8):1400-140, Jan. 1960.
Smith and Fuzek, "Catalytic Hydrogenation of Furan and Substituted Furans on Platinum," J. Am. Chem. Soc., 71(2):415-9, Feb. 1949.
Spanjers et al., "Branched Diol Monomers from the Sequential Hydrogenation of Renewable Carboxylic Acids," ChemCatChem., 8(19):3031-5, Oct. 2016.
Tsapatsis et al., "A New, Yet Familiar, Lamellar Zeolite," ChemCatChem., 2:246-8, Mar. 2010.
Tsapatsis et al., "Pores by Pillaring: Not Always a Maze," Angew. Chem. Int. Ed., 47(23):4262-3, May 2008.
Van Koningsveld et al., "The monoclinic framework structure of zeolite H-ZSM-5. Comparison with the orthorhombic framework of as-synthesized ZSM-5", Zeolites, 10:235-42, May 1990.
Yang and Seng, "One-Step Catalytic Transformation of Carbohydrates and Cellulosic Biomass to 2,5-Dimethyltetrahydrofuran for Liquid Fuels," ChemSusChem., 3(5):597-603, May 2010.
Yim et al., "Metabolic engineering of *Escherichia coli* for direct production of 1,4-butanediol," Nat. Chem. Biol., 7(7):445-52, May 2011.
Yokoi et al.," Periodic Arrangement of Silica Nanospheres Assisted by Amino Acids," J. Am. Chem. Soc., 128(42) 13664-5, Oct. 2006.
Zhang et al., "Synthesis of Self-Pillared Zeolite Nanosheets by Repetitive Branching," Science 336(6089):1684-7, Jun. 2012.
U.S. Appl. No. 16/337,600, filed Mar. 28, 2019, Omar A. Abdelrahman, Published.

* cited by examiner

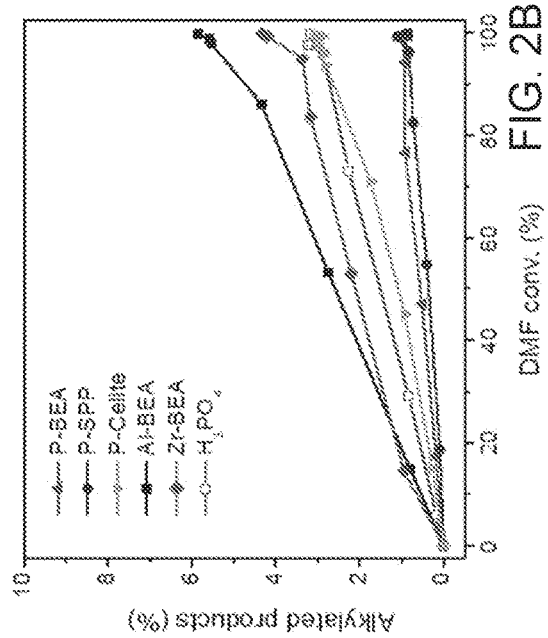
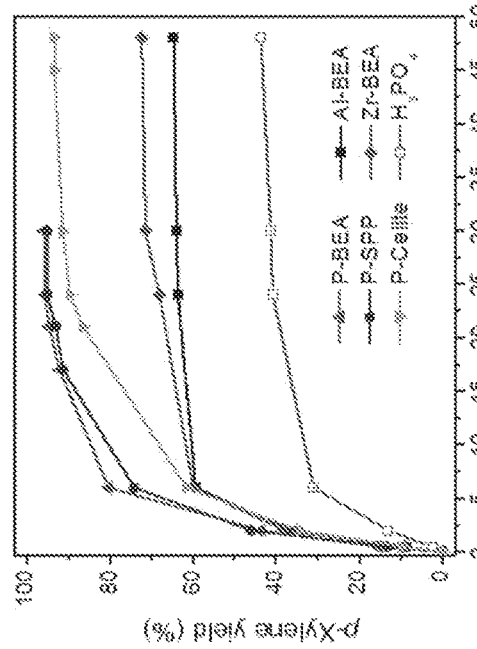
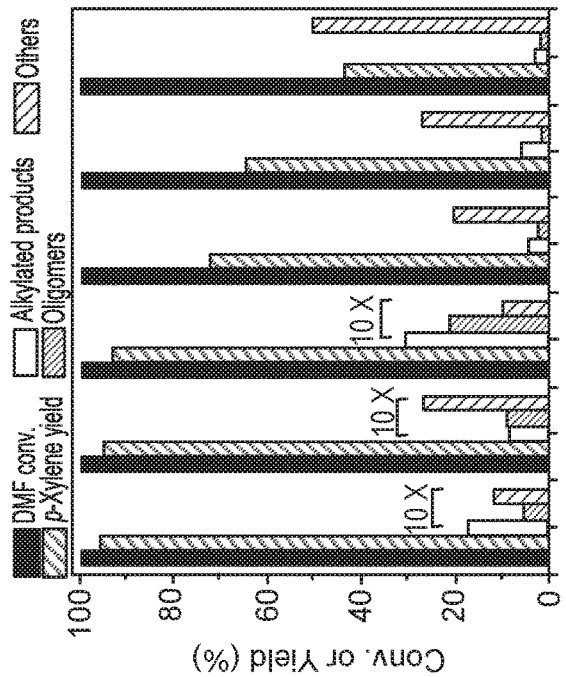
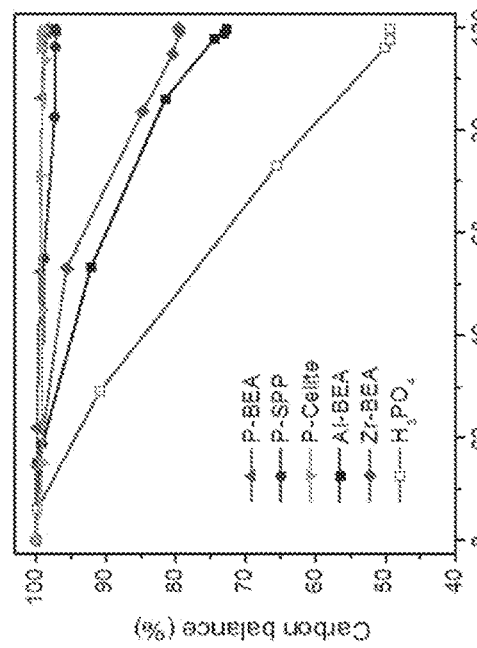

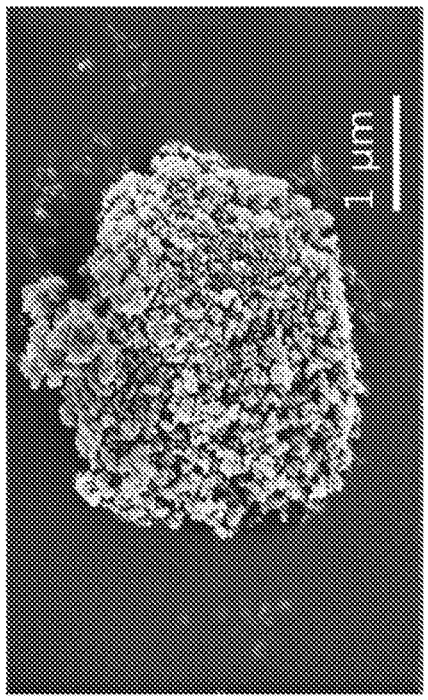
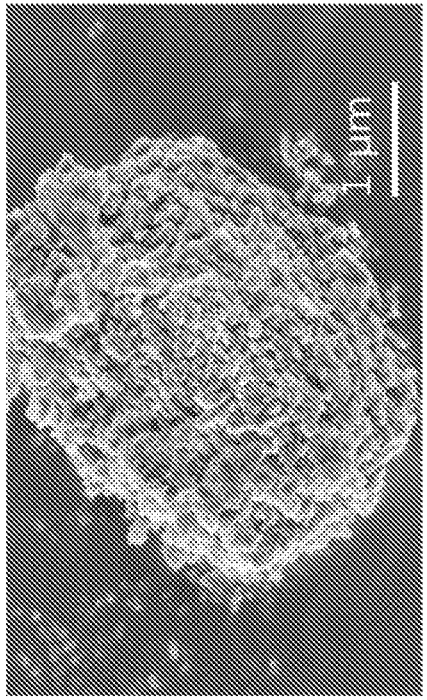
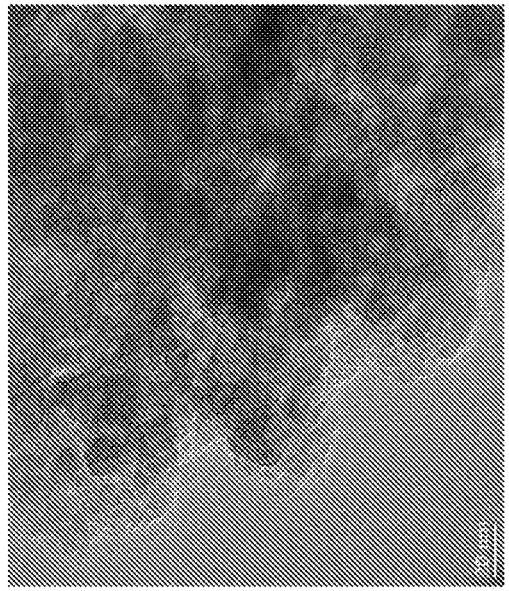

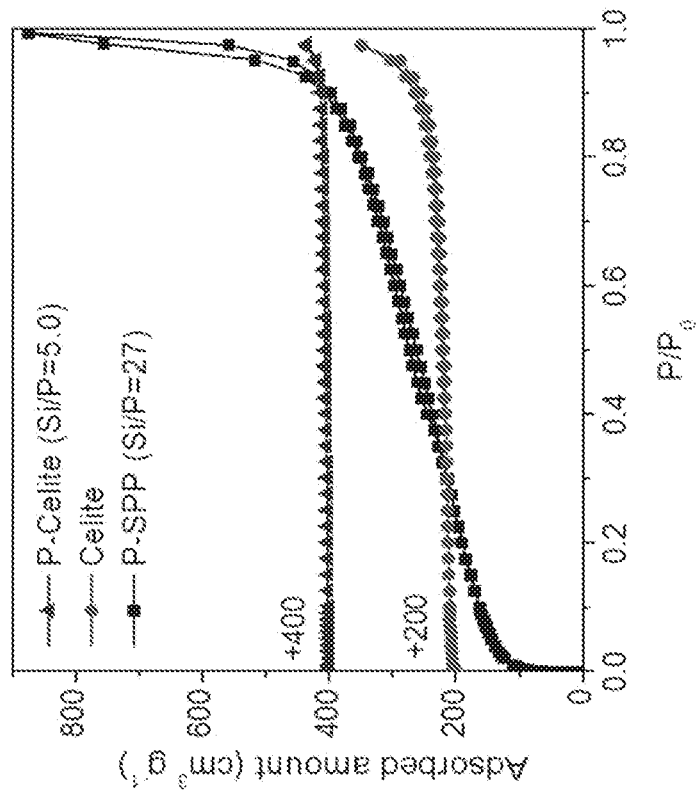
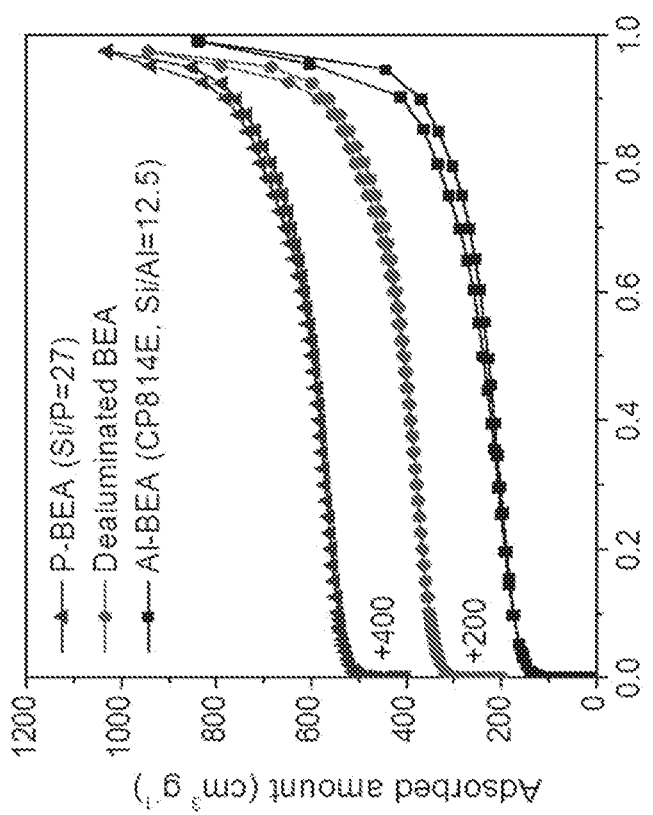
FIG. 6A
FIG. 6B

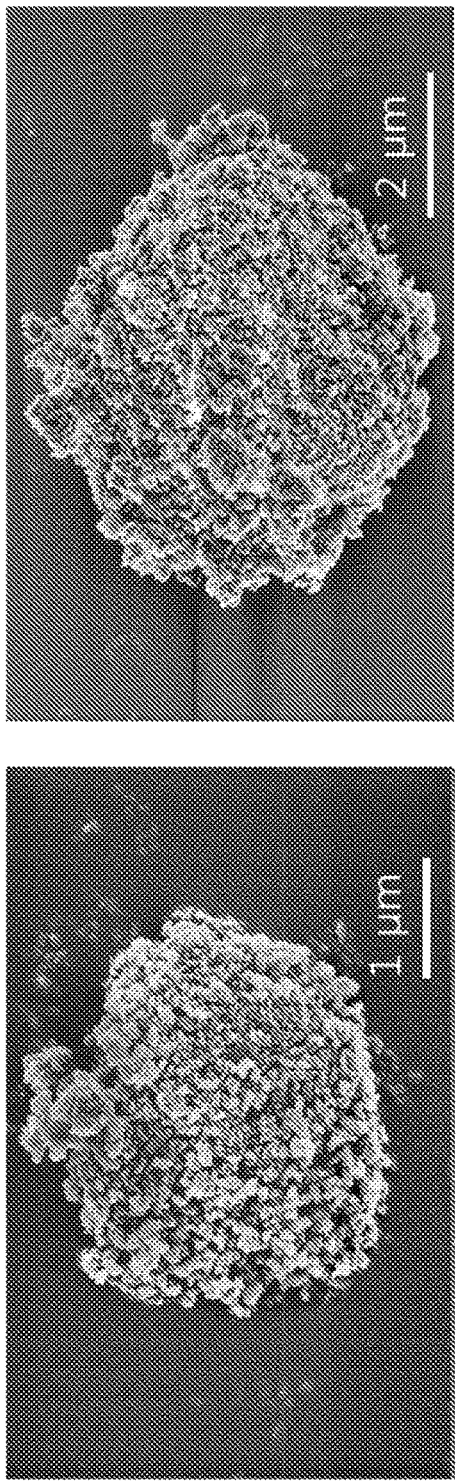
FIG. 12A
FIG. 12B
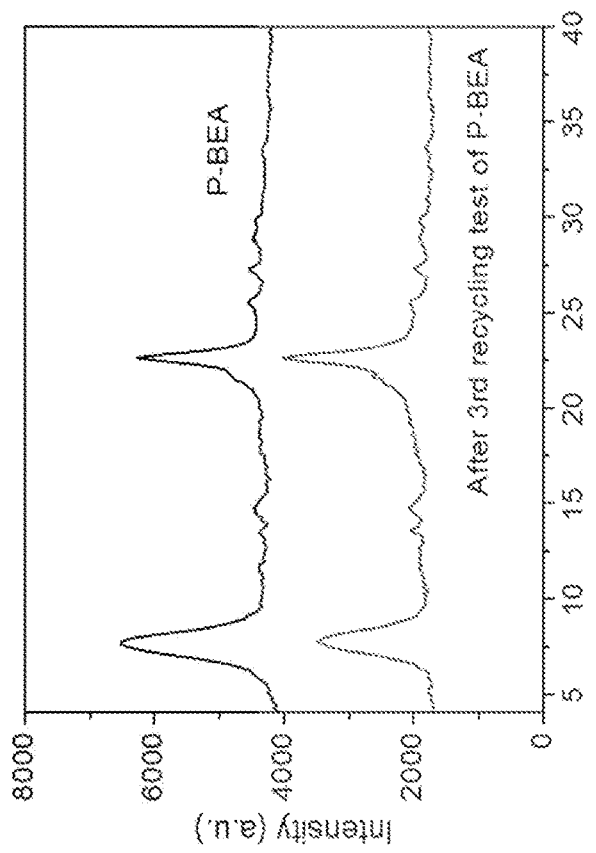
FIG. 12C

PHOSPHORUS-CONTAINING SOLID CATALYSTS AND REACTIONS CATALYZED THEREBY, INCLUDING SYNTHESIS OF P-XYLENE

CROSS-REFERENCE TO RELATED APPLICATIONS

This application is a National Stage application under 35 U.S.C. § 371 of International Application No. PCT/US2017/054558, having an International Filing Date of Sep. 29, 2017, which claims the benefit of U.S. Application Ser. No. 62/402,238 entitled "USE OF PHOSPHORUS-CONTAINING SOLID CATALYSTS" filed Sep. 30, 2016; U.S. Application Ser. No. 62/410,919 entitled "METHODS OF FORMING ISOPRENE FROM 2-METHYL-1,4-BUTANEDIOL, DERIVATIVES OR COMBINATIONS THEREOF" filed Oct. 21, 2016; U.S. Application Ser. No. 62/410,922 entitled "METHODS OF FORMING DIENES FROM TETRAHYDROFURAN, DERIVATIVES OR COMBINATIONS THEREOF" filed Oct. 21, 2016; U.S. Application Ser. No. 62/414,302 entitled "PHOSPHORUS-CONTAINING SOLID CATALYSTS AND METHODS OF USE THEREOF" filed Oct. 28, 2016; U.S. Application Ser. No. 62/419,202 entitled "METHODS OF FORMING ISOPRENE FROM 2-METHYL-1,4-BUTANEDIOL, DERIVATIVES OR COMBINATIONS THEREOF" filed Nov. 8, 2016; and U.S. Application Ser. No. 62/419,247 entitled "METHODS OF FORMING DIENES FROM TETRAHYDROFURAN, DERIVATIVES, OR COMBINATIONS THEREOF" filed Nov. 8, 2016, all of which are incorporated by reference herein in their entirety.

Application Ser. No. 62/419,247 entitled "METHODS OF FORMING DIENES FROM TETRAHYDROFURAN, DERIVATIVES, OR COMBINATIONS THEREOF" filed Nov. 8, 2016, all of which are incorporated by reference herein in their entirety.

STATEMENT OF GOVERNMENT INTEREST

This invention was made with Government support under contract number DE-SC0001004 awarded by the U.S. Department of Energy. The Government has certain rights in this invention.

BACKGROUND p-Xylene is a major product dominating current chemical production in terms of volume and energy consumption. Due to the rapid growth in the global market of polyethylene terephthalate (PET, 6-8% per year), its replacement with a renewable feedstock is a highly sought goal, and there exist numerous ongoing research and development efforts to produce p-xylene from renewable biomass feedstocks. However, current synthetic methods lead to alkylated and oligomerized products, and low yields of p-xylene.

SUMMARY

In a first general aspect, a catalyst includes a porous material, and phosphorus coupled to the porous material. The porous material can be a microporous material, a mesoporous material, or a micro-mesoporous material.

Implementations of the first general aspect include one or more of the following features.

In some implementations, the porous material is a molecular sieve framework that includes silicon and defines micropores bounded at least in part by 8-membered tetrahedral atom rings, 10-membered tetrahedral atom rings, 12-membered tetrahedral atom rings, or a combination thereof. The molecular sieve framework may include aluminum, and a ratio of silicon atoms to aluminum atoms in the molecular sieve framework may be at least 100:1, at least 300:1, at least 500:1, or at least 1000:1. A ratio of silicon atoms to phosphorus atoms may be in a range of 3:1 to 150:1. The molecular sieve framework may include zeolite beta (BEA), MFI, or self-pillared pentasil (SPP). In some cases, the porous material includes at least one zeolite selected from the group consisting of AFI, *BEA, CFI, CHA, CON, DDR, FAU, FER, GME, IFR, ISV, ITE, ITH, ITW, LTA, LTL, MAZ, MEI, MOR, MTF, MTW, MWW, OFF, RWR, SOD, STF, STO, STT, and TON. The porous material may include mesoporous silica, such as SBA-15. In certain cases, the porous material includes mesoporous graphitic carbon or a carbon molecular sieve.

In a second general aspect, dehydrating a reactant including a cyclic ether or an alcohol includes contacting the reactant with a catalyst, where the catalyst includes a phosphorus-containing porous material.

Implementations of the second general aspect may include one or more of the following features.

The reactant may be derived from biomass. In some implementations, the reactant is a cyclic ether, such as a furan. In one example, the cyclic ether is 2,5-dimethylfuran, and contacting the reactant with the catalyst includes contacting the 2, 5-dimethylfuran with ethylene in a nonaqueous solvent in the presence of the catalyst to yield a cycloadduct, and dehydrating the cycloadduct in the presence of the catalyst to yield a product including p-xylene. The yield of p-xylene may be at least 90%, at least 93%, at least 95%, at least 97%, or at least 99%. In some cases, the ethylene is formed by contacting ethanol with the catalyst to yield ethylene before contacting the 2, 5-dimethylfuran with the ethylene. In some implementations, the reactant is an alcohol. When the reactant is ethanol, contacting the ethanol with the catalyst yields a product including ethylene. When the reactant is isopropanol, contacting the isopropanol with the catalyst yields a product including propene. The catalyst may be a catalyst according to the first general aspect.

In a third general aspect, synthesizing a catalyst including phosphorus includes contacting a porous material with a phosphorus-containing compound to yield a wet porous material including phosphorus, removing water from the wet porous material including phosphorus to yield a dry porous material including phosphorus, and calcining the dry porous material including phosphorus to yield a catalyst including phosphorus coupled to the mesoporous material. The porous material may be a microporous material, a mesoporous material, or a micro-mesoporous material.

Implementations of the third general aspect may include one or more of the following features.

The porous material may be solvo-thermally synthesized in the presence of the phosphorus-containing compound to yield the wet porous material including phosphorus. The porous material may include a molecular sieve framework defining micropores bounded at least in part by 8-membered tetrahedral atom rings, 10-membered tetrahedral atom rings, 12-membered tetrahedral atom rings, or a combination thereof. Aluminum may be removed from the porous material before contacting the porous material with the phosphorus-containing compound.

In some implementations, the phosphorus-containing compound includes phosphoric acid. In certain implementations, the phosphorus-containing compound includes at least one of tetra(n-butyl) phosphonium hydroxide, tetramethyl phosphonium hydroxide, tetraethyl phosphonium hydroxide, and tetrapropyl phosphonium hydroxide. The porous material may include mesoporous silica, mesoporous graphitic carbon, or a carbon molecular sieve.

In a fourth general aspect, synthesizing p-xylene includes contacting, in the presence of a catalyst including a phosphorus-containing microporous, mesoporous, or micro-mesoporous material, biomass-derived 2,5-dimethylfuran with ethylene in a nonaqueous solvent to yield p-xylene.

In some implementations of the fourth general aspect, the contacting yields a cycloadduct, and dehydration of the cycloadduct may be catalyzed with the catalyst to yield the p-xylene.

In a fifth general aspect, synthesizing a catalyst including phosphorus includes solvo-thermally synthesizing a porous material in the presence of a phosphorus-containing compound to yield a wet porous material including phosphorus, removing water from the wet porous material including phosphorus to yield a dry porous material comprising phosphorus, and calcining the dry porous material including phosphorus to yield a catalyst including phosphorus coupled to the porous material. The porous material may be a microporous material, a mesoporous material, or a micro-mesoporous material.

Implementations of the fifth general aspect may include one or more of the following features.

In some implementations, the porous material includes a molecular sieve framework defining micropores bounded at least in part by 8-membered tetrahedral atom rings, 10-membered tetrahedral atom rings, 12-membered tetrahedral atom rings, or a combination thereof. The phosphorus-containing compound may include at least one of tetra(n-butyl) phosphonium hydroxide, tetramethyl phosphonium hydroxide, tetraethyl phosphonium hydroxide, and tetrapropyl phosphonium hydroxide.

Catalysts and processes described herein provide increased efficiency for the production of p-xylene from renewable biomass feedstocks, thereby increasing the economic feasibility of the production of p-xylene from biomass, such as cellulose.

BRIEF DESCRIPTION OF THE DRAWINGS

FIG. 2A is a bar graph and FIGS. 2B-2D are line graphs showing the catalytic activities for the p-xylene production from the reaction of 2,5-dimethylfuran (DMF) with ethylene. FIGS. 2A-2D show overall product distributions, yield of alkylated by-products, carbon balance, and yield of p-xylene, respectively. Reaction conditions were as follows: 1.35 M DMF in n-heptane; 250° C.; 62 bar ethylene; DMF/P (mol mol$^{-1}$)=100 for P-BEA, P-SPP, P-Celite and H$_3$PO$_4$; 4.0 mM acid for Al-BEA and Zr-BEA. Reaction times for all catalysts were 48 hours, except 24 hours for P-BEA and P-SPP.

FIGS. 5A and 5B are scanning electron microscope (SEM) images of Al-BEA (Zeolyst, CP814E, Si/Al=12.5) and P-BEA, respectively, and FIGS. 5C and 5D are transmission electron microscope (TEM) images of P-SPP and P-BEA, respectively.

FIG. 6A shows argon adsorption-desorption isotherms for P-BEA, dealuminated BEA and Al-BEA, and FIG. 6B shows argon adsorption-desorption isotherms for P-CELITE, CELITE, and P-SPP.

FIGS. 12A and 12B are SEM images and FIG. 12 C is an XRD pattern of fresh P-BEA and spent P-BEA after a third recycling test.

DETAILED DESCRIPTION

Figure 1:
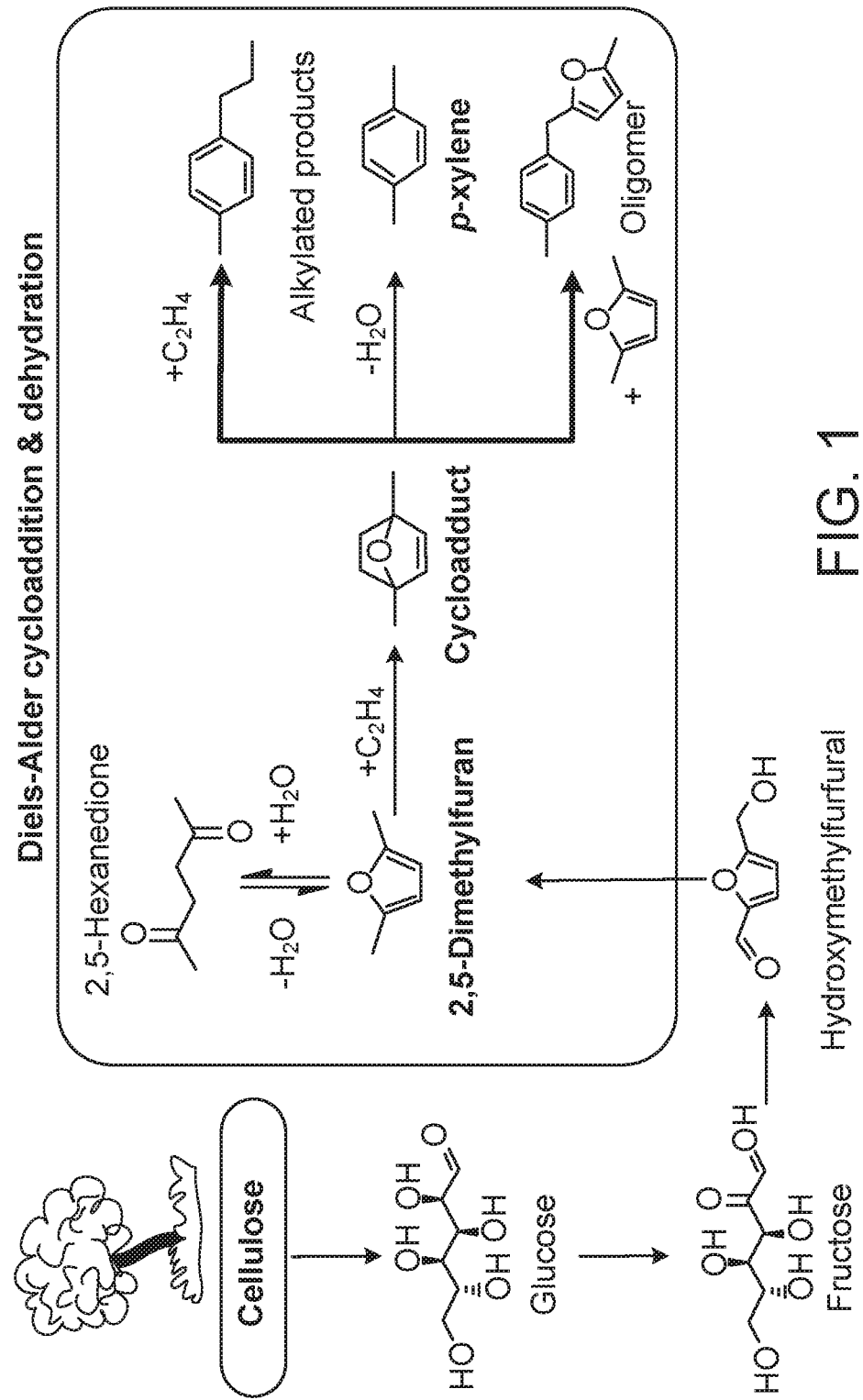
FIG. 1 depicts production of renewable p-xylene.

FIG. 1 depicts a reaction pathway for the production of p-xylene from renewable cellulose. Glucose is produced by the depolymerization and hydrolysis of cellulose. Isomerization of glucose to fructose is then performed using enzymes or thermochemical catalysts including base or Lewis acid heterogeneous catalysts such as Sn-BEA. Fructose is then converted to 5-hydroxymethylfurfural (HMF), and further hydrodeoxygenated to form dimethylfuran (DMF). The last step to generate p-xylene is the Diels-Alder cycloaddition of DMF and ethylene, followed by subsequent dehydration of the cycloadduct intermediate. This reaction offers a completely renewable pathway for p-xylene formation, since DMF and ethylene can be obtained from glucose and bio-ethanol dehydration, respectively. Increasing the efficiency of the reaction from DMF and ethylene to p-xylene is a factor in economic feasibility of the production of p-xylene from cellulose. Analysis of the process of FIG. 1 suggests that a cost reduction of about 20% can be achieved by increasing the p-xylene yield from 70% to 90%.

FIG. 1 depicts three side reactions that compete with the pathway to p-xylene, including (a) hydrolysis of DMF to form 2, 5-hexanedione, (b) multiple additions of ethylene to form alkylated aromatic chemicals, and (c) dimerization of the furan feedstock and/or aromatic products to form oligomers. Density functional theory (DFT) calculations have highlighted the benefit of using Brønsted acids for promotion of the main pathway and facilitating a high yield of p-xylene. However, these Brønsted acid zeolites also catalyze alkylation and isomerization reactions, which not only lower p-xylene yield, but also lead to fast catalyst deactivation. Lewis acid zeolites (e.g., Zr-BEA and Sn-BEA) are also active for the production of p-xylene from DMF with an initial formation rate of p-xylene comparable to that of Brønsted acidic Al-BEA.

Methods described herein include contacting a reactant with porous, phosphorus-containing catalyst to dehydrate the reactant. The reactant may be a cyclic ether (e.g., DMF) or an alcohol (e.g., ethanol or ispropanol). Contacting may occur in the presence of a nonaqueous solvent. Suitable reaction conditions include a temperature in a range between 200° C. and 400° C., or between 250° C. and 300° C.

Phosphorus-containing solid catalysts and methods for catalyzing tandem Diels-Alder cycloaddition and dehydration of biomass-derived DMF and ethylene to renewable p-xylene using phosphorus-containing solid catalysts are disclosed herein, along with methods of dehydrating alcohols with the phosphorus-containing solid catalysts to yield alkenes.

As disclosed herein, DMF and ethylene are contacted in a nonaqueous solvent in the presence of a phosphorus-containing solid catalyst that is essentially devoid of strong Brønsted acid character under conditions sufficient to produce p-xylene without catalyzing other by-product reactions, such as alkylation and oligomerization reactions. Examples of solid acid catalysts that are essentially devoid of Brønsted acid character include dealuminated Brønsted acidic aluminosilicate zeolites. Dealuminated Brønsted acidic aluminosilicate zeolites can have a Si/Al atomic ratio greater than 100, greater than 1,000, or greater than 10,000. Other examples of solid acid catalysts that are essentially devoid of Brønsted acid character include zeolites synthesized directly without addition of aluminum in the synthesis mixtures or under conditions that do not lead to aluminum incorporation. In some embodiments, an alcohol (e.g., ethanol) or is contacted with phosphorus-containing solid catalysts to yield an alkene (e.g., ethylene) without catalyzing other by-product reactions.

Suitable nonaqueous solvents include non-polar solvents (e.g., heptane), polar solvents (e.g., dioxane), polar aprotic solvents (e.g., tetrahydrofuran) and polar protic solvents (e.g., isopropanol).

Suitable phosphorus-containing catalysts include a porous inorganic material having phosphorus coupled to the porous material. As used herein, "porous material" generally includes microporous material, mesoporous material, and micro-mesoporous material, where "microprous material" refers to a material having pores with a diameter less than about 2 nm (micropores), "mesoporous material" refers to a material having pores with a diameter in a range of about 2 nm to about 50 nm (mesopores), and "micro-mesoporous material" (or "hierarchical material") refers to a material having micropores and mesopores. Examples of suitable microporous materials include BEA, MFI, and microporous zeolites. Examples of suitable mesoporous materials include silica gel and BP2000. Examples of suitable micro-mesoporous materials include mesoporous zeolites and hierarchical zeolites, such as self-pillared pentasil (SPP). In some cases, the porous material is a nanomaterial, with at least one dimension in a range of 1 nm to 1000 nm, or 1 nm to 100 nm. The phosphorus coupled to the porous material may be covalently bonded to the mesoporous material, impregnated in the mesoporous material, or both.

In some embodiments, the mesoporous material is a molecular sieve framework including silicon and defining micropores bounded at least in part by 8-membered tetrahedral atom rings, 10-membered tetrahedral atom rings, 12-membered tetrahedral atom rings, or a combination thereof. The molecular sieve framework may include aluminum, and a ratio of silicon atoms to aluminum atoms in the molecular sieve framework is typically at least 100:1, at least 300:1, at least 500:1, or at least 1000:1. In some cases, a ratio of silicon atoms to phosphorus atoms in the molecular sieve framework is in a range of 1:1 to 1000:1 or 3:1 to 150:1. In some examples, the molecular sieve framework includes zeolite beta (BEA), MFI, or self-pillared pentasil (SPP). In some examples, the molecular sieve framework includes at least one zeolite selected from the group consisting of AFI, *BEA, CFI, CHA, CON, DDR, FAU, FER, GME, IFR, ISV, ITE, ITH, ITW, LTA, LTL, MAZ, MEI, MOR, MTF, MTW, MWW, OFF, RWR, SOD, STF, STO, STT, and TON.

In some embodiments, the porous material includes porous silica. The porous silica may be microporous silica, mesoporous silica, or micro-mesoporous silica. Suitable examples include surfactant templated mesoporous silica (e.g., SBA-15), silica nanoparticles, hierarchical (micro-mesoporous) single unit cell zeolites (e.g., SPP), and nanozeolites (e.g., zeolites having a particle size less than about 100 nm).

In some embodiments, the porous material includes mesoporous carbon material such as graphitic carbon or a carbon molecular sieve. Suitable examples include graphene, carbon nanotubes, disordered carbons, ordered mesoporous carbon, and BP-2000.

Synthesizing a phosphorus-containing porous material described herein includes contacting a porous material with a phosphorus-containing compound to yield a wet phosphorus-containing porous material, removing water from the wet phosphorus-containing porous material to yield a dry phosphorus-containing porous material, and calcining the dry phosphorus-containing porous material to yield a catalyst having phosphorus coupled to the porous material. As described herein, the porous material may include a molecular sieve framework defining micropores bounded at least in part by 8-membered tetrahedral atom rings, 10-membered tetrahedral atom rings, 12-membered tetrahedral atom rings, or a combination thereof. In some cases, aluminum is removed from the molecular sieve framework before the molecular sieve framework is contacted with the phosphorus-containing compound. Other suitable porous materials include micro-mesoporous nanosilica and mesoporous graphitic carbon and carbon molecular sieves.

In one example, the phosphorus-containing compound is phosphoric acid. In other examples, the phosphorus-containing compound is an organic structure-directing agent (OSDA), such as tetra(n-butyl) phosphonium hydroxide, tetramethyl phosphonium hydroxide, tetraethyl phosphonium hydroxide, tetrapropyl phosphonium hydroxide.

Synthetic methods include dehydrating an oxygen-containing compound by contacting the oxygen-containing compound with phosphorus-containing catalysts described herein.

In some embodiments, the oxygen-containing compound is a cyclic ether, such as DMF. Contacting DMF with ethylene in a nonaqueous solvent in the presence of the catalyst yields a cycloadduct, and the cycloadduct is dehydrated in the presence of the catalyst to yield a product including p-xylene. A yield of the p-xylene is typically at least 90%, at least 93%, at least 95%, at least 97%, or at least 99%. The total yield of by-products, such as hexanedione, alkylated aromatic chemicals, and oligomers is typically less than 10%, less than 7%, less than 5%, less than 3%, or less than 1%. In some cases, before contacting the DMF and the ethylene, ethanol is contacted with the catalyst to yield ethylene. The ethylene then undergoes Diels-Alder cycloaddition with the DMF.

In some embodiments, the oxygen-containing compound is an alcohol. Examples of suitable alcohols include butanol, ethanol, and propanol (e.g., isopropanol). Contacting the alcohol with the phosphorus-containing catalyst yields an alkene. For example, contacting butanol with the phosphorus-containing catalyst yields butane, contacting ethanol with the phosphorus-containing catalyst yields ethylene, and contacting propanol with the phosphorus-containing catalyst yields propene.

In some embodiments, the oxygen-containing compound is a weak acid, such as lactic acid, and contacting lactic acid with the phosphorus-containing catalyst yields acrylic acid.

EXAMPLES

Synthesis of p-Xylene

To improve p-xylene yield, two phosphorus-containing siliceous zeolites, zeolite Beta (BEA) and self-pillared pentasil (SPP) zeolite were tested. These phosphorus-containing siliceous zeolites are inactive for alkylation and oligomerization reactions. The phosphorus-containing zeolite catalysts are not only active for p-xylene production but also lead to high yields. Phosphorus-containing zeolites are highly active, selective and stable catalysts. Phosphorus-containing BEA zeolite (P-BEA) with 12 membered-ring (12 MR) structures and phosphorus-containing self-pillared pentasil (P-SPP) zeolite nanosheets with 10 membered-ring (10 MR) structures exhibit activities up to 97% yield of p-xylene at 99% conversion of DMF.

Figure 4:
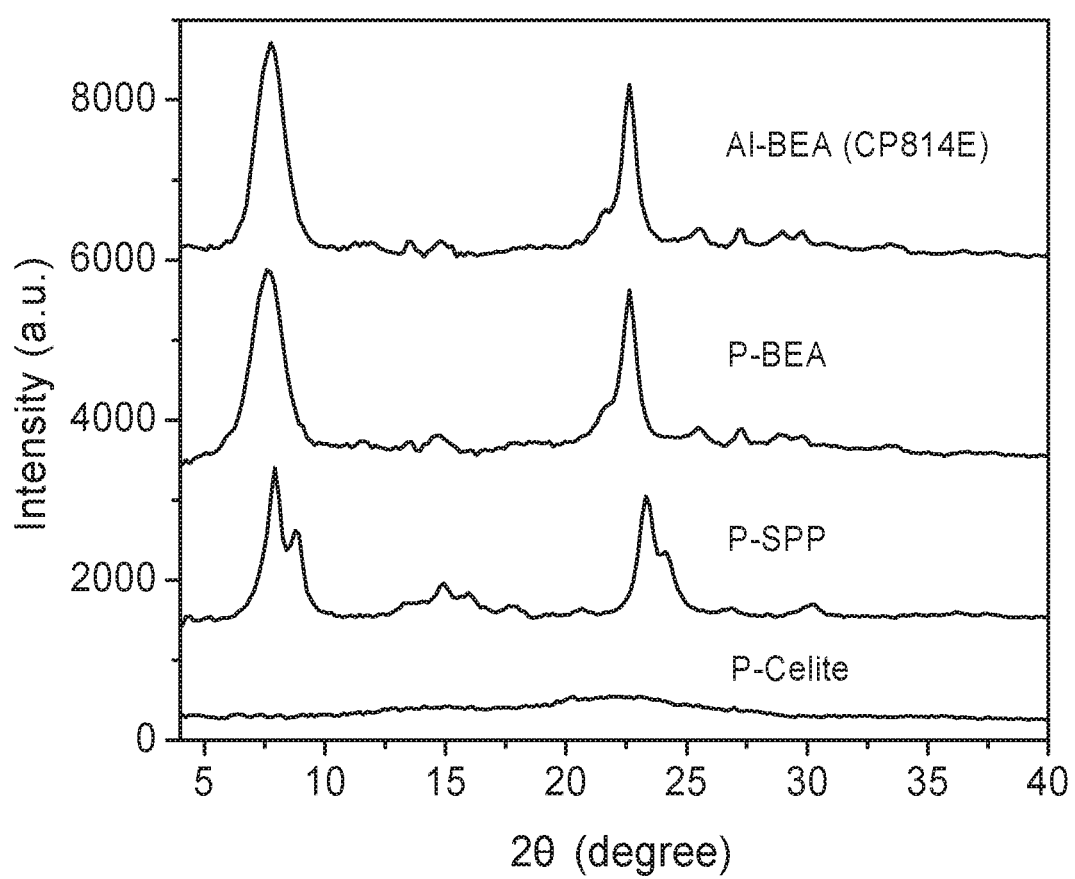
FIG. 4 shows powder X-ray diffraction (XRD) patterns of Al-BEA (Zeolyst, CP814E, Si/Al=12.5), P-BEA, P-SPP and P-CELITE.

Phosphorus-containing zeolite Beta (P-BEA) was synthesized by a post-synthetic route, according to which P was incorporated within zeolite BEA by calcining dealuminated zeolite BEA after impregnation with phosphoric acid ($H_3PO_4$). The synthesis procedure includes the dealumination of Al-BEA (Zeolyst, CP814E, Si/Al=12.5) using nitric acid, the impregnation of $H_3PO_4$ on the dealuminated zeolite BEA and the incorporation of phosphorus within the zeolite by calcination. The crystal structure and morphology of the zeolite BEA were preserved after the incorporation of phosphorus, as evidenced by their XRD patterns (FIG. 4) and SEM images (FIGS. 5A and 5B) and TEM images (FIGS. 5C and 5D). The micropore volume and BET specific surface area of the zeolite after the incorporation of phosphorus are 0.10 cm$^3$ g$^{-1}$ and 499 m$^2$ g$^{-1}$, respectively, suggesting the high surface area and microporous structures were retained during the phosphorus modification step (FIGS. 6A and 6B and Table 1).

TABLE 1

ICP analysis, quantity of Brønsted acid sites, and textural properties of various samples

| Catalyst | Si/P[a] (mol mol$^{-1}$) | Si/Al[a] (mol mol$^{-1}$) | IPA adsorbed[c] (μmol g$^{-1}$) | Micropore volume[d] (cm$^3$ g$^{-1}$) | Surface area[e] (m$^2$ g$^{-1}$) | Total pore volume[f] (cm$^3$ g$^{-1}$) |
|---|---|---|---|---|---|---|
| P-BEA | 27.1 | 1471 | 99 | 0.10 | 499 | 0.801 |
| DeAl-BEA | — | 1465 | — | 0.07 | 508 | 0.946 |
| Al-BEA | — | 12.5[b] | 620 | 0.15 | 563 | 1.069 |
| P-SPP | 27.3 | N.D.[g] | 173 | 0.08 | 598 | 1.114 |
| P-Celite | 5.0 | 13.3 | N.D.[g] | 0.00 | 12 | 0.045 |

[a]Determined by ICP.
[b]Data from supplier.
[c]Determined by IPA-TPD.
[d]t-plot method obtained from Ar Adsorption-desorption isotherms.
[e]BET surface area obtained from Ar Adsorption-desorption isotherms.
[f]Calculated from the amount adsorbed at P/P$_0$ = 0.97 in Ar Adsorption-desorption isotherms.
[g]N.D. means 'Not detected'.

Phosphorus-containing self-pillared pentasil (P-SPP) was synthesized by a direct synthesis method using tetrabutylphosphonium hydroxide (TBPOH) as an organic structure-directing agent (OSDA). After crystallization, the formed SPP zeolite containing the OSDA was subjected to calcination, resulting in the decomposition of the OSDA and incorporation of phosphorus within the zeolite (Table 1). In contrast, the use of tetrabutylammonium hydroxide (TBAOH) as the OSDA leads to SPP zeolite free of phosphorus active sites. The crystallinity and morphology of P-SPP are similar to those of pure silica SPP displaying orthogonally connected single-unit cell lamellae of MFI, as evidenced by the XRD patterns, TEM images and argon adsorption isotherms (FIGS. 4, 5A-5D, 6A, and 6B). The rotational intergrowths of single-unit-cell lamellae leads to repetitive branching nanosheets. The nanosheets can be about 2 nm thick and can contain a network of micropores having a diameter of about 0.5 nm. The house-of-cards arrangement of the nanosheets creates a network mesopores having a diameter in a range of about 2 nm to about 7 nm. For comparison, a commonly used phosphorus-based catalyst, P-CELITE, was also examined. It is a solid phosphoric acid (SPA) catalyst synthesized by impregnation of $H_3PO_4$ on celite (diatomaceous silica), a commercially available amorphous silica material (FIGS. 4, 5A-5D, 6A, and 6B, Table 1).

Figure 7A:
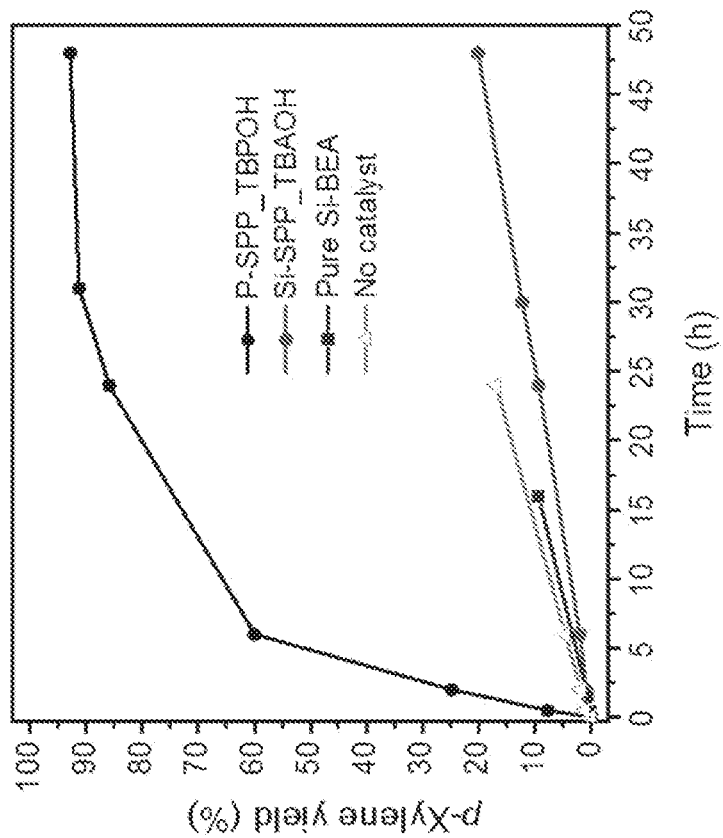
FIGS. 7A and 7B are graphs showing DMF conversion and p-xylene yield, respectively, for the reaction of DMF with ethylene w over P-SPP made using tetra (n-butyl) phosphonium hydroxide (TBPOH), Si-SPP made using tetra (n-butyl) ammonium hydroxide (TBAOH), pure siliceous BEA and no catalyst. Reaction conditions were as follows: 50 mL of 1.35 M DMF in n-heptane, 250° C., 62 bar ethylene, 0.228 g catalyst.
Figure 7B:
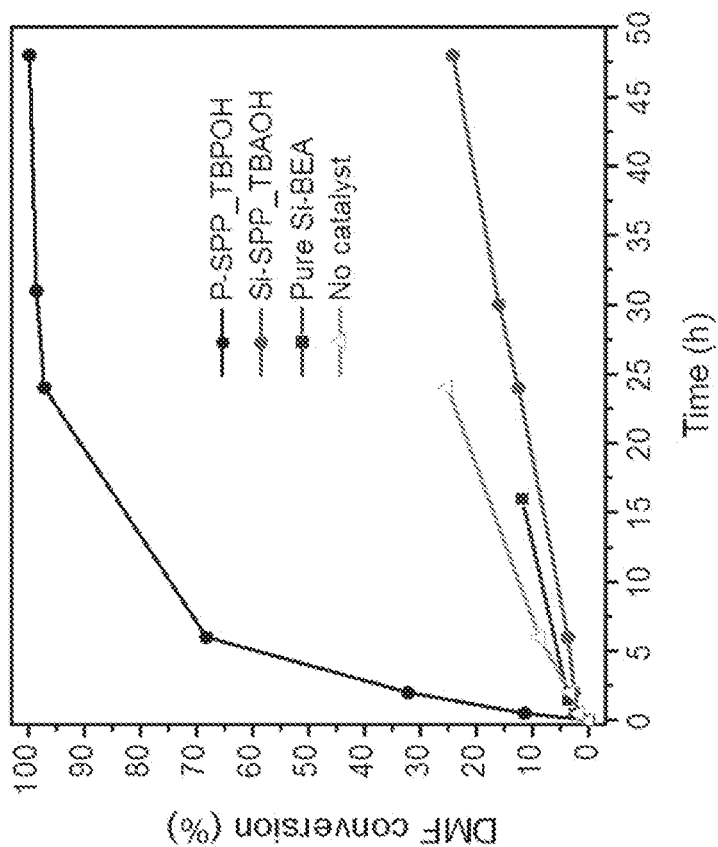
Figure 8A:
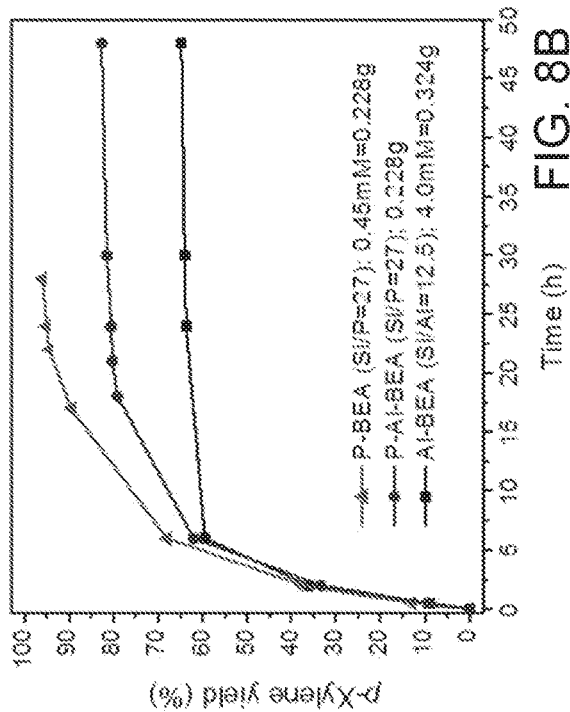
FIGS. 8A-8D are graphs showing catalytic performances of P-Al-BEA and CELITE for the production of p-xylene. Reaction conditions were as follows: 1.35 M DMF in n-heptane, 250° C., 62 bar ethylene.
Figure 8B:
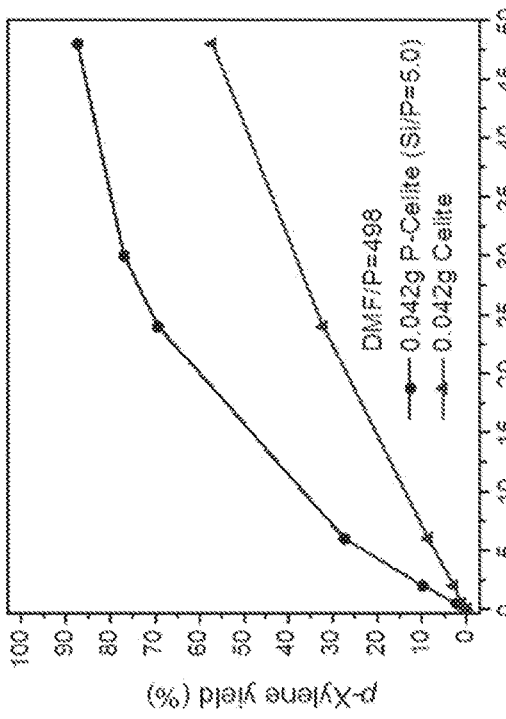
Figure 8C:
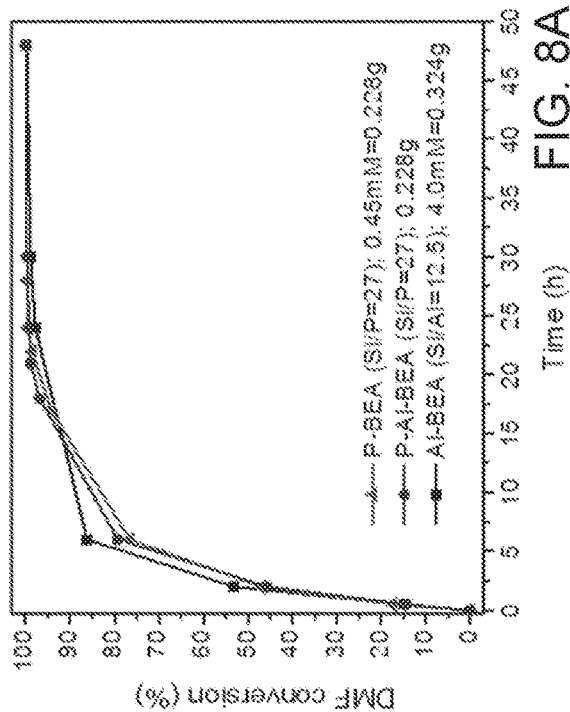
Figure 8D:
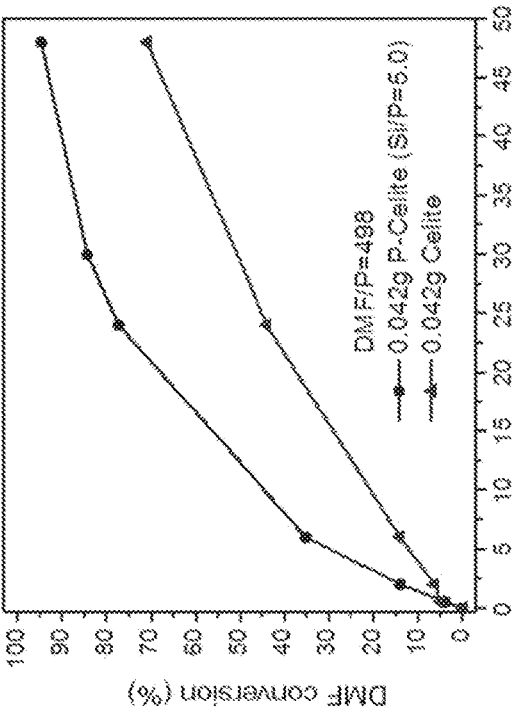

FIGS. 2A-2D show the results obtained from reacting DMF with ethylene over the phosphorus-containing solid catalysts and other Brønsted and Lewis acid zeolites as well as a homogeneous acid catalyst, $H_3PO_4$, under the same acid concentration (4.0 mM for both Brønsted and Lewis acid sites) or the same DMF/P molar ratio=100 at 250° C. The phosphorus-containing catalysts are capable of catalyzing the reaction to some extent to produce p-xylene (FIG. 2A). In the absence of phosphorus, the same zeolites (all-silica SPP (Si-SPP) made using TBAOH and siliceous Beta (Si-BEA)) did not exhibit detectable catalytic activity (FIGS. 7A and 7B). Among the catalysts, P-BEA (Si/P=27) and P-SPP (Si/P=27) exhibited superior performances with excellent yield (97%) of p-xylene at 99% DMF conversion (FIG. 2A). Although not intending to be held to theory, the superior performance of P-BEA and P-SPP could be attributed to the large micropores of P-BEA and the highly branched hierarchical micro-mesoporous structure of P-SPP, respectively, which provide efficient dispersion of the active sites and facile transport of reactants and products. The non-zeolitic phosphorus-based solid catalyst, P-CELITE (Si/P=5.0), exhibited a p-xylene yield of about 90%, lower than those obtained from P-BEA and P-SPP. The yields of p-xylene from Brønsted acid, Al-BEA, and Lewis acid, Zr-BEA, were much lower, 65% and 72% at 99% DMF conversion, respectively. The homogeneous $H_3PO_4$ catalyst was also active for the reaction but with a much lower yield to p-xylene (i.e., 39% at 99% DMF conversion). In addition, a control experiment was conducted over phosphorus-containing Al-BEA made by impregnation of phosphorus on Al-BEA using the same post-synthetic method. The low yield to p-xylene over this catalyst compared to P-BEA (FIGS. 8A-8D) suggests that the modification of phosphorus on siliceous zeolites advantageously facilitates high-yield production of p-xylene.

Figure 9A:
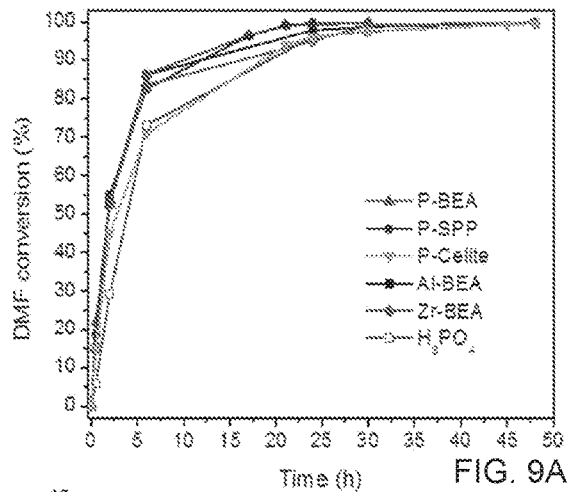
FIGS. 9A-9E are graphs showing catalytic activities for the p-xylene production from the reaction of DMF with ethylene, including DMF conversion (FIG. 9A) and overall product distributions (FIGS. 9B-9E). Reaction conditions were as follows: 1.35 M DMF in n-heptane; 250° C.; 62 bar ethylene; DMF/P (mol mol-1)=100 for P-BEA, P-SPP, P—Celite and H$_3$PO$_4$; 4.0 mM acid for Al-BEA and Zr-BEA.
Figure 9B:
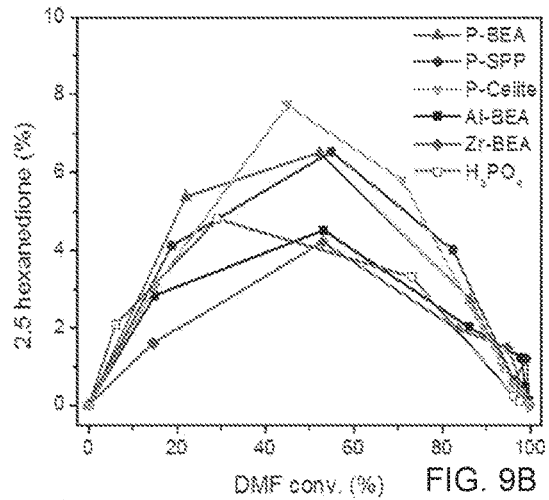
Figure 9C:
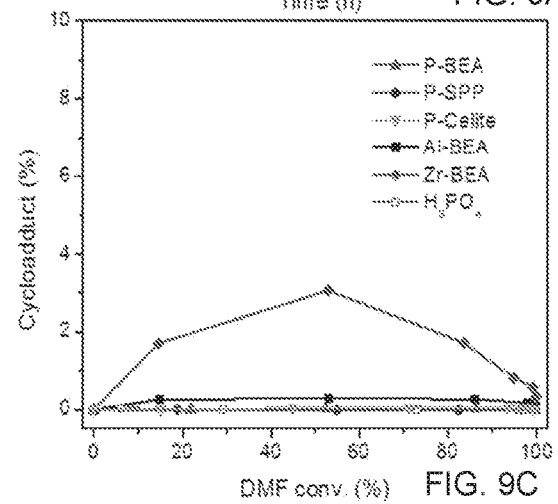
Figure 9D:
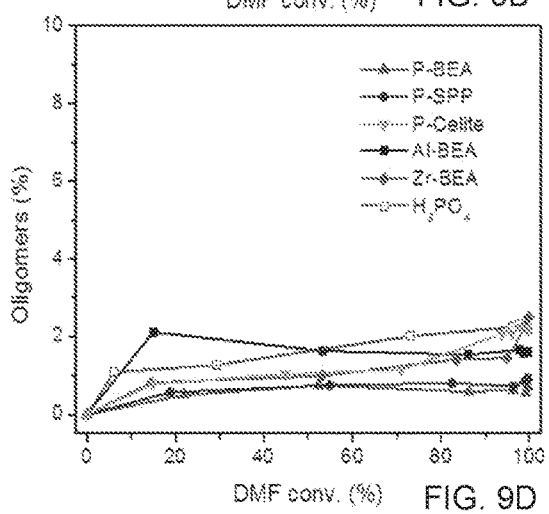
Figure 9E:
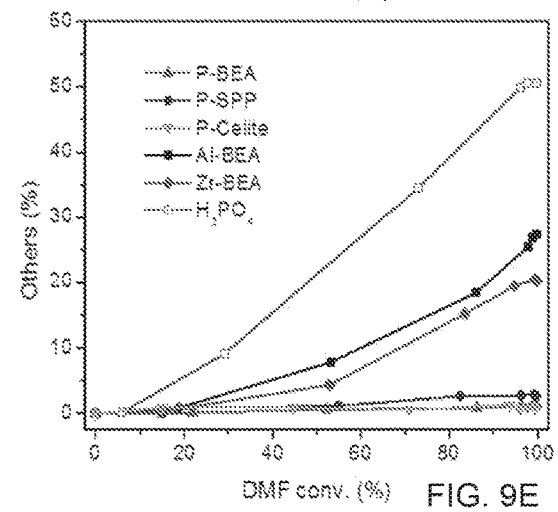
Figure 10A:
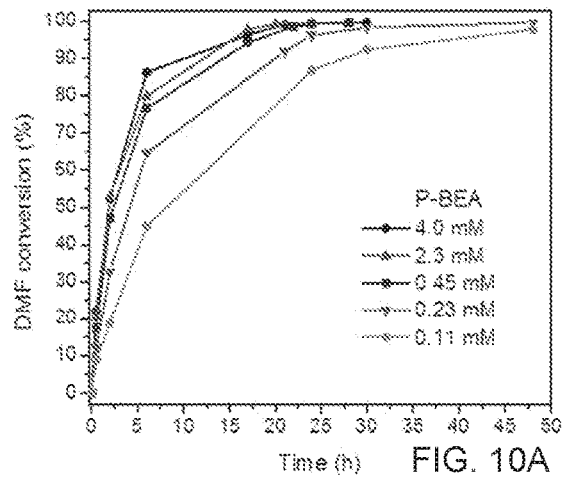
FIGS. 10A-10J are graphs showing the effect of acid site concentration on the catalytic performance for p-xylene production from the reaction of DMF with ethylene: P-BEA (FIGS. 10A-10B), P-SPP (FIGS. 10D-10D), P-CELITE (FIGS. 10E-10F), Al-BEA (FIGS. 10G-10H), and Zr-BEA (FIGS. 10I-10J). Reaction conditions were as follows: 1.35 M DMF in n-heptane, 250° C., 62 bar ethylene.
Figure 10B:
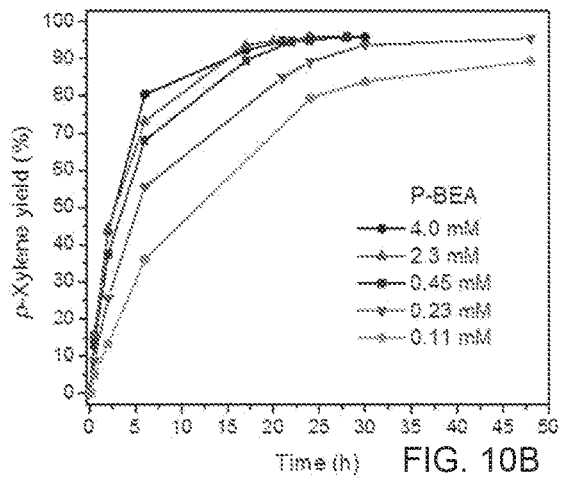
Figure 10C:
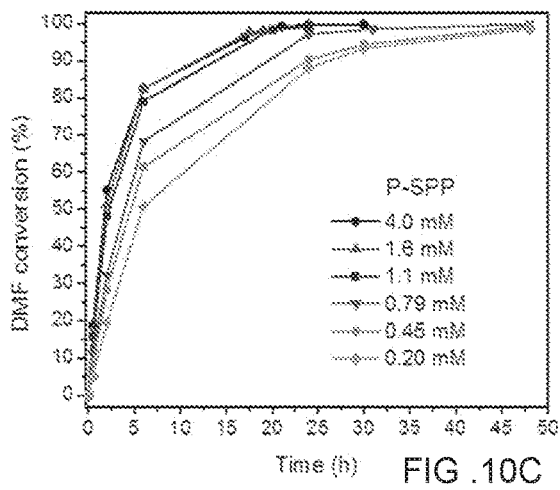
Figure 10D:
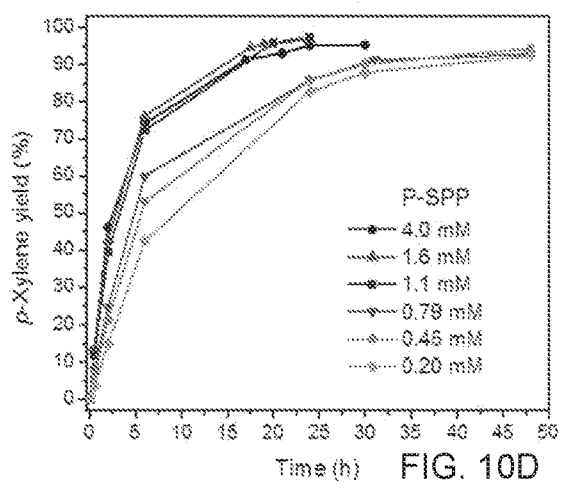
Figure 10E:
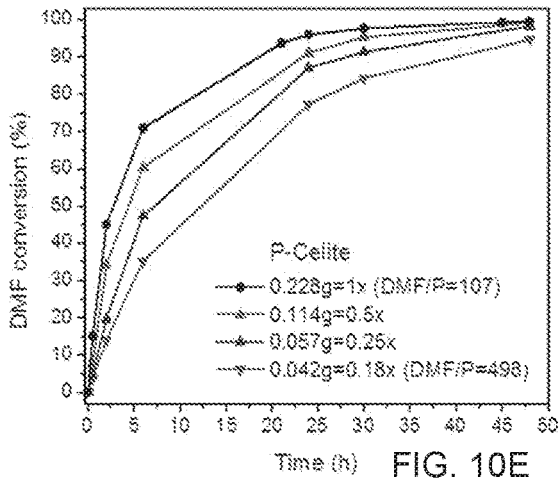
Figure 10F:
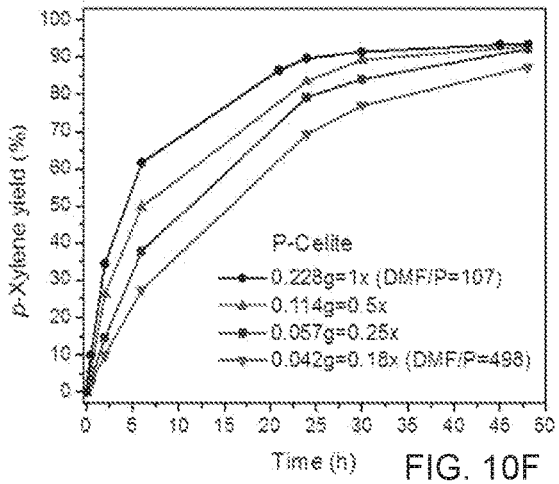
Figure 10G:
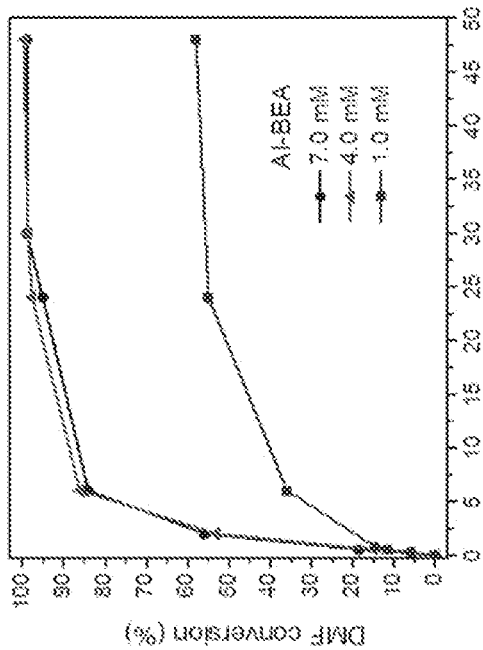
Figure 10H:
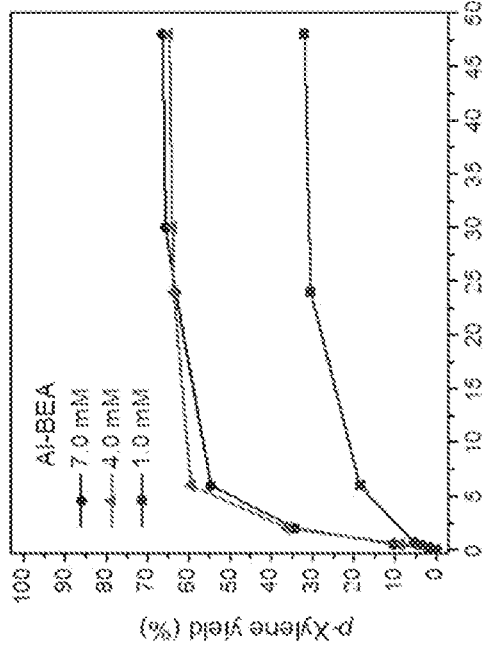
Figure 10I:
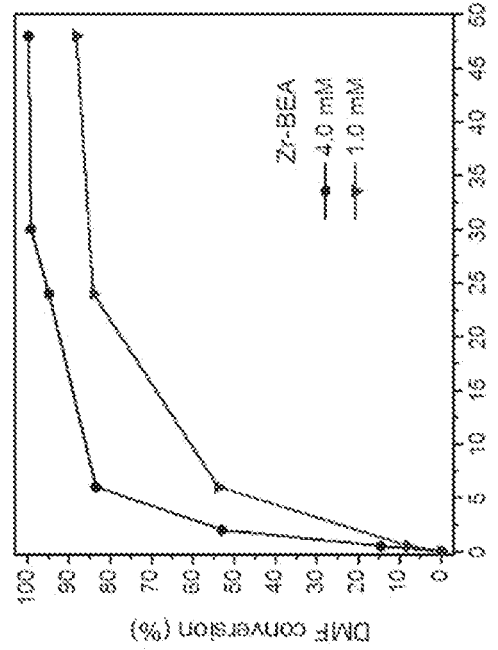
Figure 10J:
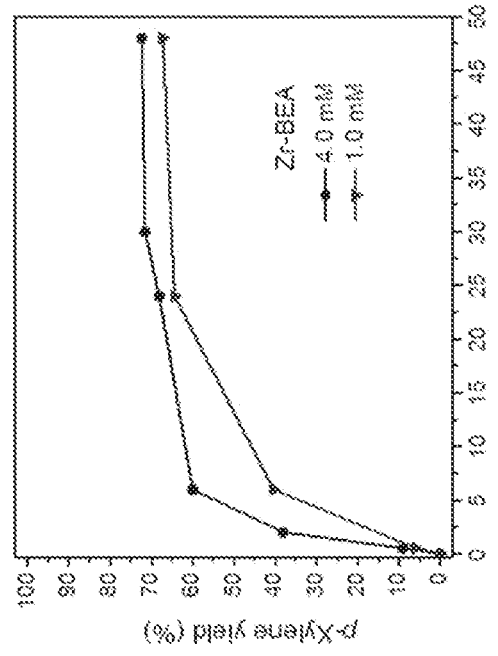

To further illustrate the performance of the phosphorus-containing catalysts, the temporal profile of the yield to p-xylene with reaction time, carbon balance and by-products versus DMF conversion are shown in FIGS. 2B and 2C. The superior performance of the phosphorus-containing catalysts is due at least in part to the much lower amounts of by-products such as alkylated aromatic chemicals and undetectable products formed during the reaction. On the other hand, Al-BEA, Zr-BEA and $H_3PO_4$ produced much more alkylated and oligomerized products with rapid reduction of quantified carbon (i.e., lower carbon balance) (FIGS. 2B and 2C, FIGS. 9A-9E). Although the DMF can be fully converted over Al-BEA, Zr-BEA and $H_3PO_4$, the p-xylene yield did not increase after six hours of the reaction time (FIGS. 2D and 9A). This is likely due to coke formation on the active sites of the catalysts, leading to significant deactivation. It is proposed that the P—OH groups on the phosphorus-containing catalysts have weaker Brønsted acidity than Al—OH—Si sites in Al-BEA and, while not able to promote these side reactions, still remain active for the dehydration reaction to produce p-xylene. It should be noted that the p-xylene yields with Al-BEA and Zr-BEA are not further improved by changing the amount of catalyst in the reactor, as shown in FIGS. 10G-10J.

Figure 3A:
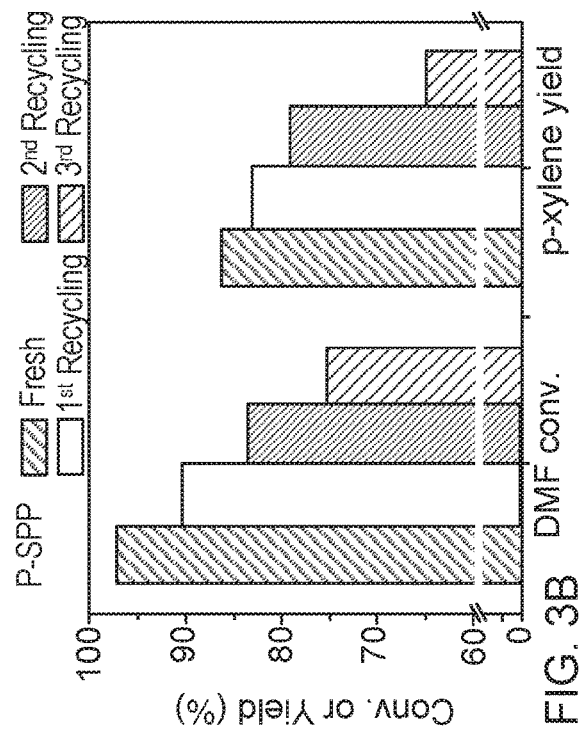
FIGS. 3A-3C are bar graphs showing the reusability of P-BEA and P-SPP, and FIG. 3D are $^{31}$P solid state magic-angle spinning (MAS) nuclear magnetic resonance (NMR) spectra of P-BEA, P-SPP and P-CELITE. Reaction conditions were as follows: 50 mL of 1.35 M DMF in n-heptane; 250° C.; 62 bar ethylene; DMF/P (mol mol$^{-1}$)=498 for P-BEA and P-SPP; 24 hours. For catalyst reusability, the spent catalyst was washed with n-heptane, dried, and calcined at 550° C. for 12 hours.
Figure 3B:
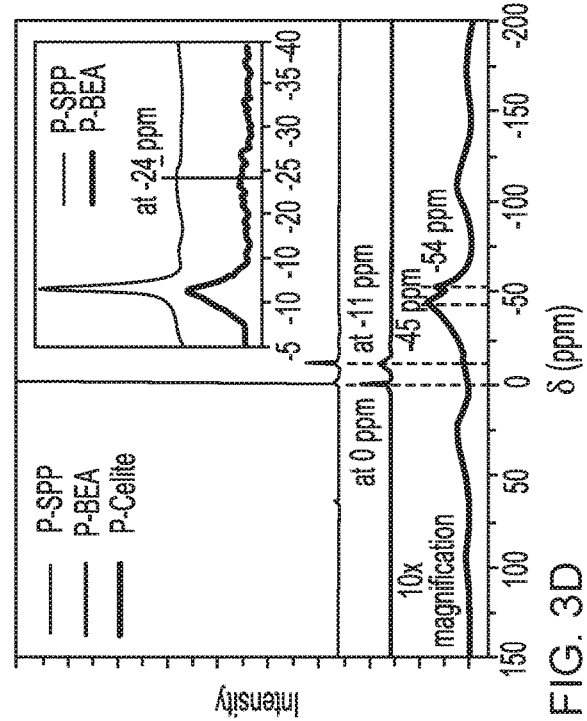
Figure 3C:
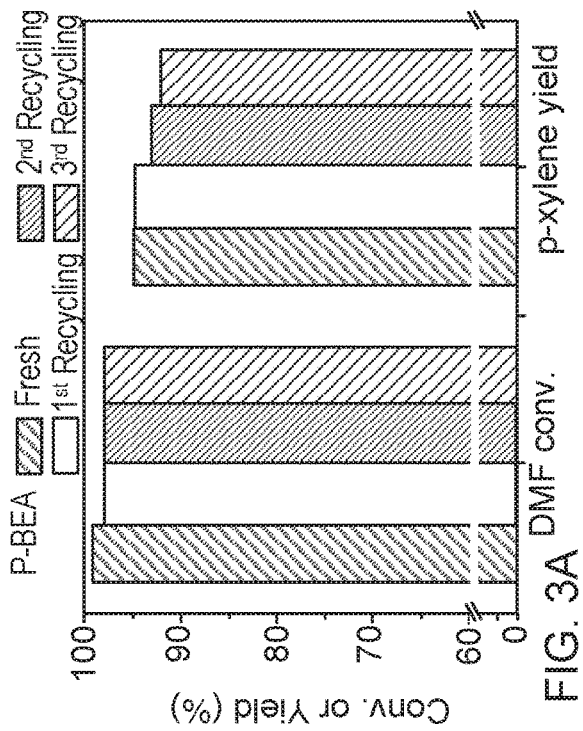
Figure 11A:
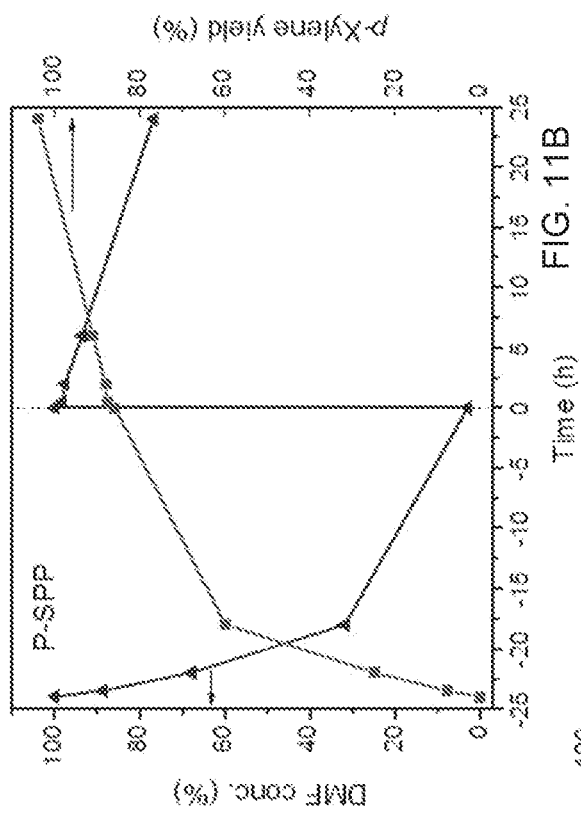
FIGS. 11A-11D are graphs showing the heterogeneous nature of the DMF reaction with ethylene over P-BEA and P-SPP. Reaction conditions are as follows: 50 mL of 1.35 M DMF in n-heptane, 250° C., 62 bar ethylene, 0.45 mM for P-BEA and 0.79 mM for P-SPP, 24 hours. To demonstrate the heterogeneous reaction, the spent catalyst was removed from the reactor and fresh DMF was filled at 0 hour on the plots in FIGS. 11A and 11B, followed by the reaction occurring for an additional 24 hours. The DMF conversion and p-xylene yield obtained from the experiments were similar to the blank experiments, indicating the reaction is heterogeneously catalyzed.
Figure 11B:
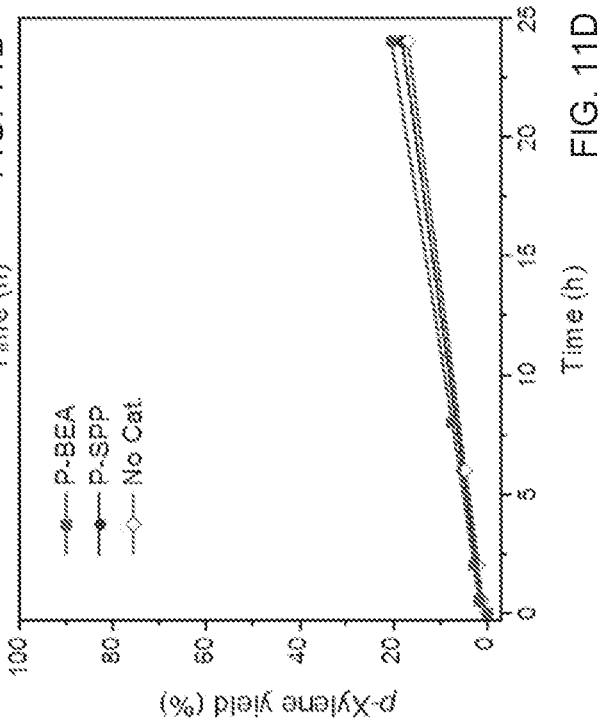
Figure 11C:
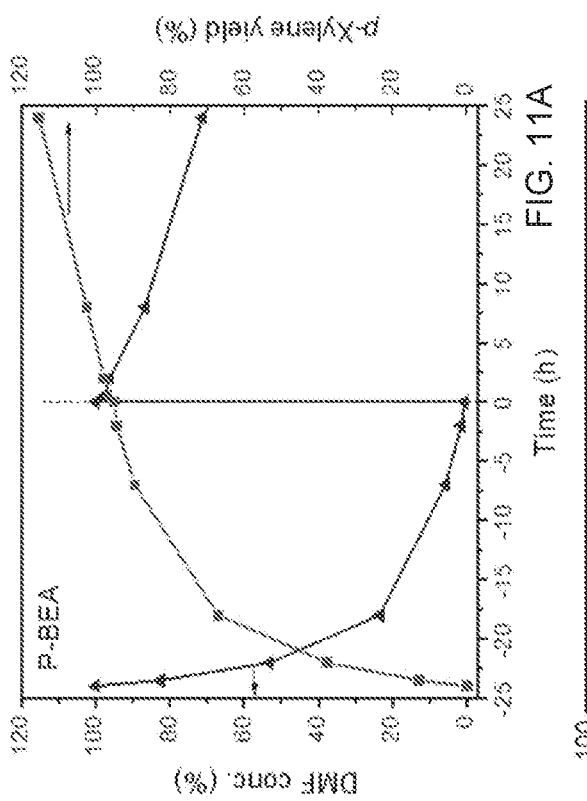
Figure 11D:
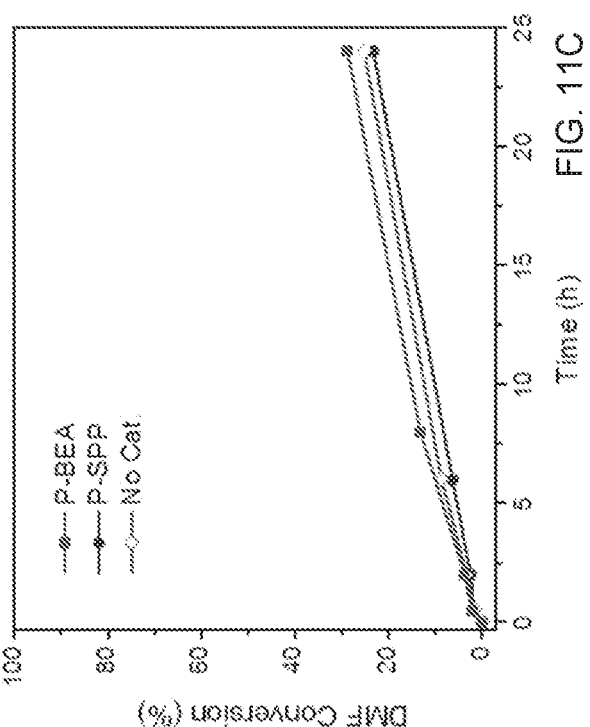

To verify the heterogeneous nature of the phosphorus catalytic sites, catalyst removal and recycle tests were conducted. In the catalyst removal test, the reaction of DMF was performed after separating the spent P-BEA catalyst from the reaction mixture. As shown in FIGS. 11A-11B, upon the removal of the catalyst, the reaction shows almost the same reaction rate as a control experiment without a catalyst, indicating that the catalytic activity observed may be attributed to the solid catalyst (FIGS. 11C-11D). In FIG. 3A, the reusability test of the P-BEA catalyst shows a high selectivity to p-xylene (94%) at 98% conversion of DMF after the third recycling test. There were no significant changes in structure of P-BEA catalyst during the recycling test, as confirmed by SEM and XRD measurement (FIGS. 12A-12C). On the contrary, p-xylene yield from P-SPP is reduced after sequential recycling (FIG. 3B). By the third recycle, DMF conversion decreased to 76% with a p-xylene yield of 65% (FIG. 3C).

Figure 3D:
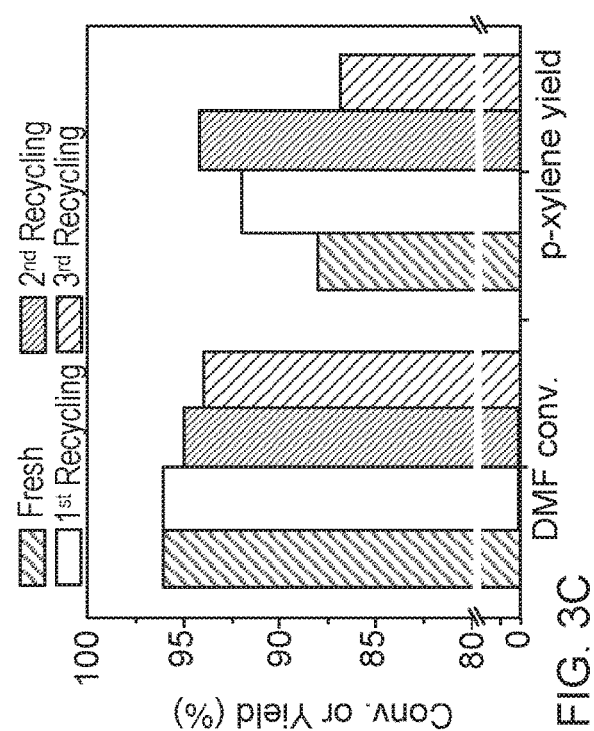

$^{31}P$ solid state magic-angle spinning (MAS) nuclear magnetic resonance (NMR) was performed to gain an insight into the chemical interaction of phosphorus with the silicate frameworks of the phosphorus-containing catalysts. As shown in FIG. 3D, P-BEA and P-SPP exhibited three main signals at 0 ($Q^0$), −11 ($Q^1$) and −24 ($Q^2$) ppm that could be assigned to free $H_3PO_4$ not chemically bonded to silicate matrices, O=P(OSi or OP)(OH)$_2$ and O=P(OSi or OP)$_2$(OH), respectively. The relative peak area for the P-BEA was 35% for $Q^0$, 46% for $Q^1$, and 19% for $Q^2$, while P-SPP exhibited 68% for $Q^0$, 26% for $Q^1$, and 6% for $Q^2$, suggesting that P was more effectively incorporated in the dealuminated BEA than to Si-SPP. In contrast, P-CELITE exhibited two main resonance peaks at −45 ($Q^4$) and −54 ppm, corresponding to $PO_4$ tetrahedra (oligomers of phosphorus) and silicon pyrophosphate ($SiP_2O_7$), respectively. Although all the three phosphorus-containing catalysts are active for the p-xylene production, phosphorus speciation by NMR is distinctly different. The enhanced catalytic efficiency of P-BEA and P-SPP (Table 2) could arise from the presence of isolated phosphorus sites, which are not dominant in the conventional solid phosphoric acid catalyst (i.e., P-CELITE). It appears that the selective phosphorus-containing zeolite materials disclosed here are a class of acidic zeolite catalysts suitable for other dehydration and acid-catalyzed reactions.

TABLE 2

Comparison of catalytic activities for the DMF reaction with ethylene[a]

| Catalyst | DMF/P (mol mol$^{-1}$) | Production rate of p-xylene[b,c] (mM h$^{-1}$ g$^{-1}$) | DMF conv.[c] at 24 h (%) | p-xylene yield[c] at 24 h (%) | p-xylene selectivity at 24 h (%) |
|---|---|---|---|---|---|
| P-BEA | 56 | 207 (±11) | 99 (±0.7) | 97 (±1.1) | 96 |
| P-SPP | 98 | 308 (±17) | 100 (±0.3) | 95 (±1.3) | 96 |
| P-CELITE | 107 | 1175 (±75) | 96 (±1.1) | 90 (±1.5) | 94 |
| P-Silica gel | 498 | 535 | 92 | 79 | 86 |
| P-35 nm SNP | 498 | 250 | 78 | 68 | 87 |
| P/Si-BEA | 498 | 1355 | 97 | 90 | 92 |
| $H_3PO_4$ | 56 | 568 | 96 | 41 | 42 |
| Si-SPP | — | 61 | 13 | 9 | 75 |

TABLE 2-continued

Comparison of catalytic activities for the DMF reaction with ethylene[a]

| Catalyst | DMF/P (mol mol$^{-1}$) | Production rate of p-xylene[b,c] (mM h$^{-1}$ g$^{-1}$) | DMF conv.[c] at 24 h (%) | p-xylene yield[c] at 24 h (%) | p-xylene selectivity at 24 h (%) |
|---|---|---|---|---|---|
| Si-BEA | — | 26 (±7.5) | 12 (±2.3)[d] | 9 (±2.4)[d] | 80[d] |
| P-SBA-15 | 56 | 197 | 92 | 90 | 94 |

[a]Reaction conditions are as follows: 50 mL of 1.35M DMF in n-heptane, 250° C., 62 bar ethylene.
[b]Reaction time: 30 min.
[c]95% confidence interval in parentheses.
[d]Reaction time: 16 h.

The phosphorus-containing zeolite materials are also active and selective for alcohol dehydration reactions. The dehydration of ethanol on P-SPP has been compared to ZSM-5, an aluminum containing zeolite. As shown in Table 3, at 400° C., with a flow rate of 30 mL/min and ethanol concentration of 8.15×10-6 mol/mL, 100% conversion of ethanol was achieved. P-SPP exhibited 96% selectivity to ethylene with a carbon balance of 98%. However, ZSM-5 exhibited 50.7% selectivity to ethylene with many other olefins and aromatics (24.3% to propylene, 11.6% to butene, 0.6% to pentene, and 12.7% to aromatics). The carbon balance for ZSM-5 is 74%, indicating significant coke formation on the ZSM-5 catalysts. It is believed the high selectivity to ethylene and slow catalyst deactivation is due at least in part to the acid sites from the phosphorus species.

TABLE 3

Comparison of catalytic activities for ethanol dehydration[a]

| Catalyst | EtOH/ catalyst (mol g$^{-1}$) | Production rate of ethylene (mol/g/min) | EtOH conv.[c] (%) | Ethylene selectivity | Carbon balance |
|---|---|---|---|---|---|
| P-SPP | 0.014 | 0.0013 | 100 | 96% | 98% |
| ZSM-5 | 0.071 | 0.0027 | 100 | 50.7% | 74% |

[a]Reaction conditions are as follows: 1 mL/h of ethanol in 30 mL/min He, 400° C., 1 atm. WHSV = 19.7 h$^{-1}$ for ZSM-5 and 3.9 h$^{-1}$ for P-SPP.
[b] Reaction time: 10 min.

Phosphorus-containing carbons (phosphorus on BP2000 carbon) and phosphorus supported on the meso-microprous silicate SBA-15 can also be selective catalysts. Table 4 lists results obtained with BP-2000 and phosphorus on SBA-15.

TABLE 4

Comparison of catalytic activities for the DMF reaction with ethylene in this study[a].

| Catalyst | DMF/P (mol mol$^{-1}$) | Production rate of p-xylene[b,c] (mM h$^{-1}$ g$^{-1}$) | DMF conv.[c] at 24 h (%) | p-xylene yield[c] at 24 h (%) | p-xylene selectivity at 24 h (%) |
|---|---|---|---|---|---|
| P-SBA-15 | 56 | 197 | 92 | 90 | 94 |
| P-BP2000 | 28 | 98 | 90 | 91 | 90 |

[a]Reaction conditions are as follows: 50 mL of 1.35M DMF in n-heptane, 250° C., 62 bar ethylene.
[b]Reaction time: 30 min.
[c]95% confidence interval in parentheses.
[d]Reaction time: 16 h.

The phosphorus-containing catalysts can also be used as catalysts for alcohol dehydration. Table 5 shows vapor phase isopropanol dehydration over several phosphorus-containing catalysts with P-MFI and P-SPP being among the more active catalysts. Reaction conditions for the dehydration reactions summarized in Table 5 were as follows: 130° C., 30 torr isopropanol, helium carrier gas (25 sccm), catalysts calcined in-situ at 550° C. with a ramp of 5° C./min, total system pressure of 1.1 bar.

TABLE 5

Vapor phase isopropanol dehydration over phosphorous supported catalysts

| Catalyst | Rate (μmol g$^{-1}$ min$^{-1}$)[a] |
|---|---|
| P-SPP | 2.1 |
| P-MFI | 2.1 |
| P-Stober | 0.6 |
| P-CHA | 0.6 |
| P-SBA15 | 0.5 |
| P-BEA (F)[b] | 0.4 |
| P-MCM-41 | 0.2 |
| P-BEA (F—EtOH)[c] | 0.2 |
| P-ZnO | 0 |

[a]Rate is defined as the total dehydration to both propene and diisopropyl ether
[b]BEA framework prepared using the fluoride method
[c]BEA framework prepared using the fluoride method, with a mixture of water and ethanol used as the impregnating solution Synthesis of Phosphorus-Containing BEA Zeolite (P-BEA)

Commercial zeolite Al-BEA (Zeolyst, CP814E, Si/Al=12.5) was dealuminated by treatment with 70 wt % nitric acid (HNO$_3$, Fisher Scientific). Typically, 0.5 g of the Al-BEA was mixed with 25 mL of 70 wt % HNO$_3$ in a TEFLON-lined stainless steel autoclave. The autoclave was then put into an 80° C. oven for 24 h under a static condition. The dealuminated zeolite BEA (DeAl-BEA) was washed extensively with deionized water and dried overnight at 100° C. Wet impregnation was performed by stirring DeAl-BEA and the appropriate amount of 85 wt % phosphoric acid (H$_3$PO$_4$, Sigma-Aldrich) in deionized water. The impregnated sample was dried 90° C. overnight, followed by calcination in a tube furnace with dry air to 600° C. for 25 min.

Synthesis of P-SPP

P-SPP was prepared by adding tetra(n-butyl) phosphonium hydroxide (TBPOH, 40 wt %, Sigma-Aldrich) as a structure-directing agent (SDA) dropwise into tetraethylorthosilicate (TEOS, 98%, Sigma-Aldrich) under stirring. To this mixture, deionized water was then added and stirred for 24 h. The mixture became a clear sol with composition 1 $SiO_2$:0.3 TBPOH:10 $H_2O$:4 EtOH. The sol was sealed in a TEFLON-lined stainless steel autoclave and heated for 3 days in an oven at 115° C. Si-SPP can be prepared with tetra(n-butyl)ammonium hydroxide solution (TBAOH, 40 wt %, Sigma-Aldrich) instead of TBPOH. After crystallization, the solid product was washed with deionized water by centrifugation and decanting of the supernatant. This process was repeated until the pH of the final supernatant was less than 9. Subsequently, the collected sample was dried at 90° C. overnight and calcined in a tube furnace at 550° C. for 12 h under dry air. Without further treatment P-SPP is directly synthesized. The phosphorus content can be adjusted by washing with water and/or by impregnation with phosphoric acid followed by calcination.

Synthesis of P-CELITE

P-CELITE was prepared through an impregnation method. First, CELITE S (Diatomaceous silica, Sigma-Aldrich) was calcined at 500° C. for 5 h under air. Then, 1 g of the calcined CELITE was ion-exchanged with 100 mL of 0.2 M $NH_4NO_3$ solution at 60° C. for 20 h. The resulting product was filtered and washed by deionized water thoroughly, followed by drying overnight. The solid was calcined at 500° C. for 5 h under air. Thereafter, 1 g of the calcined powder was mixed with 4 mL of 0.75 M $H_3PO_4$ solution, and then dried at 90° C. overnight. The dried mixture was calcined at 500° C. for 5 h under air.

Synthesis of P-Al-BEA

P-Al-BEA was prepared by impregnation of $H_3PO_4$ on zeolite Al-BEA (Zeolyst, CP814E, Si/Al=12.5), according to the same procedure described in the preparation of P-BEA.

Synthesis of siliceous BEA (Si-BEA)

Pure Si-BEA was synthesized as described in M. A. Camblor, A. Corma, S. Valencia, Spontaneous nucleation and growth of pure silica zeolite-beta free of connectivity defects, Chemical Communications, 2365-66 (1996). Typically, 8.72 g of tetraethylammonium hydroxide (TEAOH, 35 wt %, Alfa Aesar or SACHEM) was mixed in 1.24 g of deionized water. To this mixture, tetraethylorthosilicate (TEOS, 98%, Sigma-Aldrich) was added and stirred for 7 h at room temperature. Thereafter, 0.86 g of HF (48%, Sigma-Aldrich) was added, and the mixture became a white solid with composition 1 $SiO_2$:0.54 TEAOH:0.54 HF:7.25 $H_2O$. The resulting solid was sealed in a TEFLON-lined stainless steel autoclave, followed by crystallization for 2 days in an oven at 140° C. Subsequently, the solid product was extensively washed with deionized water by vacuum filtration. The collected sample was dried at 90° C. overnight and calcined in a tube furnace at 550° C. for 12 h under dry air.

Syntheses of P-Silica Gel, P-35 nm Silica Nanoparticles (P-35 nm SNP) and P/Si-BEA Wet impregnation was performed by stirring the silica matrix of interest and the appropriate amount of 85 wt % phosphoric acid ($H_3PO_4$, Sigma-Aldrich) in deionized water. Three different silica materials were used: 1) silica gel (DAVISIL Grade 636, Sigma-Aldrich), 2) monodisperse silica nanoparticles with 35 nm size, synthesized as described in T. Yokoi, Y. Sakamoto, O. Terasaki, Y. Kubota, T. Okubo and T. Tatsumi, Periodic Arrangement of Silica Nanospheres Assisted by Amino Acids, Journal of the American Chemical Society, 128, 13664-13665 (2006), and 3) pure siliceous BEA zeolite (Si-BEA). The resulting impregnated sample was dried 90° C. overnight, followed by calcination in a tube furnace with dry air to 600° C. for 25 min.

Synthesis of P-SBA-15 (Si/P=27)

Mesoporous SBA-15 was synthesized as described in Sayari, A.; Han, B.-H.; Yang, Y., Simple Synthesis Route to Monodispersed SBA-15 Silica Rods. J. Am. Chem. Soc. 2004, 126, 14348-14349. Pluronic P-123 was added to a well-mixed solution of deionized water and HCl. TEOS was then added to this solution with a composition of 1 $SiO_2$:5.7 HCl:0.017 P-123:192.7 $H_2O$. The solution was stirred for five minutes and then maintained at 308 K under static conditions for 20 h. Following this, the solution was maintained at elevated temperatures under static conditions for 24 h. The temperature during this step determined the microporosity and mesoporosity of the synthesized SBA-15 rods. Three SBA-15 samples were synthesized at temperatures of 308 K during this step, respectively. The product was collected by filtration and washed with deionized water followed by drying at 343 K for 10 h. To remove the surfactant, the sample was calcined at 823 K for 12 h with a ramping rate of 0.5 K/min under flowing dry air. Wet impregnation was performed by stirring 0.4 g of synthesized SBA-15 and the 18.2 mL of 85 wt % phosphoric acid ($H_3PO_4$, Sigma-Aldrich) in 3.33 mL of deionized water. The impregnated sample was dried 90° C. overnight, followed by calcination in a tube furnace with dry air to 600° C. for 25 min.

Synthesis of P-BP2000

Wet impregnation was performed by stirring 0.4 g of carbon black, BP2000, and 18.2 mL of 85 wt % phosphoric acid ($H_3PO_4$, Sigma-Aldrich) in 3.33 mL of deionized water. The impregnated sample was dried at 90° C. overnight, followed by calcination in a tube furnace with helium flow to 600° C. for 30 min.

Materials Characterization

Powder X-ray diffraction (XRD) patterns of the samples were recorded on an XRD diffractometer (X'Pert Pro, PANalytical) operated at 45 kV of an acceleration voltage and 40 mA of a current using Cu Kα radiation. The data were collected over 4-40° of a 2θ range. A scanning electron microscope (SEM, Magellan 400, FEI) was used to examine the morphology of the products. Prior to the SEM measurement, the samples were coated with platinum/palladium alloy. To take TEM images, aqueous suspensions of the zeolite samples were prepared. TEM specimens were made by placing droplets of the suspension onto the copper grid coated with ultra-thin carbon film and holey carbon film (Ted Pella Inc.), followed by air-drying at room temperature. TEM imaging was performed using a CCD camera on an FEI Tecnai $G^2$ F30 TEM operating at 300 kV. Elemental analysis was performed on inductively coupled plasma optical emission spectroscopy (ICP-OES, iCap 6500 Dual view, Thermo Scientific) in Analytical Geochemistry Lab, Department of Earth Sciences in University of Minnesota. Argon adsorption-desorption isotherms were measured at 87 K by using an automated gas sorption analyzer (Autosorb iQ2, Quantachrome) after the samples were degassed at 300° C. under vacuum.

In order to quantify the concentration of Brønsted acid sites on a catalyst, isopropylamine temperature program decomposition (IPA-TPD) coupled with thermogravimetric analysis was performed on a TA instrument Q500, following a procedure developed by Gorte et al. (R. J. Gorte, What do we know about the acidity of solid acids?, Catalysis Letters, 62:1-13 (1999); W. E. Farneth, R. J. Gorte, Methods for Characterizing Zeolite Acidity, Chemical Reviews, 95:615-35 (1995)). Typically, 0.01 g of catalyst was first pretreated at 550° C. for 1 h by flowing He with a rate of 100 cm$^3$ min$^{-1}$ in order to remove the water and other impurities from the catalyst surface. After the sample cooled down to 120° C., IPA was dosed into the system under a He flow. When the sample was saturated with IPA, only He flowed into the system for 1 h to eliminate weakly adsorbed IPA on the catalyst. Subsequently, system temperature was increased to 700° C. with a ramping rate of 10° C. min$^{-1}$. The total Brønsted acid site concentration was determined by the weight difference between 300° C. and 400° C., which is the temperature range where IPA decomposes into propylene and amine on the Brønsted acid sites.

Solid state NMR spectra were recorded using a Bruker DSX-500 spectrometer and a Bruker 4 mm MAS probe. The operating frequency is 202.5 MHz for $^{31}$P. Powder samples packed into 4 mm zirconia rotors were spun at ambient conditions. For MAS NMR experiments, a radiofrequency pulse of 4 μs-π/2 and strong $^1$H decoupling pulse with two pulse phase modulation (TPPM) were employed for signal averaging of $^{31}$P MAS NMR. Chemical shifts were externally referenced to concentrated $H_3PO_4$ for $^{31}$P NMR.

Diels-Alder Reaction and Dehydration of Dimethylfuran (DMF) with Ethylene

In a bench-top reactor (Parr), 50 mL of 1.35 M DMF (>98%, Alfa Aesar) in n-heptane (99%, Alfa Aesar) including 0.08 M n-tridecane (>98%, Alfa Aesar, internal standard) was mixed with the appropriate amount of a catalyst. The reactor was purged with nitrogen at room temperature under 1000 rpm of stirring. The catalyst acid concentration present in the system was defined as the total number of acid sites of the catalyst divided by the reactant volume. Subsequently, the mixture was heated to 250° C. by a 4848 temperature control unit (Parr). At 250° C., ethylene gas (Airgas) with 38 bar partial pressure was introduced into the system, and the reaction was allowed to proceed. During the entire reaction, the total pressure of the reactor was maintained at 62 bar. Time course of the reaction was monitored by taking samples (0.5 mL) for analysis at specified time intervals. The quantitative analysis of the sample was performed by Agilent 6890 gas chromatography (GC) equipped with a flame ionization detector and a Restek RTX-VMS capillary column (30.0 m length, 0.25 mm id, 1.4 μm film thickness). The products, DMF, p-xylene (>99%, Sigma-Aldrich) and 2,5-hexanedione (97%, Alfa Aesar) were identified by comparing the retention times of each standard chemical, and also cross-checked on a GC-MS system (7890B GC, Agilent). The alkylated products were quantified by using the response factor (RF) for 1-methyl-4-propylbenzene, while the oligomer contents were estimated using the additive RF of DMF and p-xylene. The concentration of cycloadduct, the intermediate produced from the Diels-Alder reaction of DMF and ethylene, was estimated by using the RF for p-xylene, following C. C. Chang et al., Lewis acid zeolites for tandem Diels-Alder cycloaddition and dehydration of biomass-derived dimethylfuran and ethylene to renewable p-xylene, Green Chem, 18:1368-76 (2016) and C. C. Chang, S. K. Green, C. L. Williams, P. J. Dauenhauer, W. Fan, Ultra-selective cycloaddition of dimethylfuran for renewable p-xylene with H-BEA, Green Chem, 16:585-88 (2014).

DMF Reaction Experiments for Heterogeneous Natures of P-BEA and P-SPP

After 24 h of 1.35 M DMF reaction with ethylene at 250° C., the spent catalyst was removed from the reaction mixture by centrifugation. To this mixture, appropriate fresh DMF was added to ensure that DMF concentration was 1.35 M in n-heptane. Next, the DMF reaction proceeded, following the procedure described herein.

Reusability Study of P-BEA and P-SPP Catalysts

After 24 h of 1.35 M DMF reaction with ethylene at 250° C., the catalyst was separated from the reaction mixture, washed with n-heptane 3 times by centrifugation, and dried at 90° C. overnight. The dried solid was calcined in a tube furnace with dry air to 550° C. for 12 h. For the 1$^{st}$ recycling test, DMF was catalyzed by the mixed catalyst (fresh catalyst:spent catalyst=2:8, weight ratio). After 24 h of the reaction, the used catalyst was treated in the same way as the one for the 1$^{st}$ recycling test. For the 2$^{nd}$ recycling test, the fresh catalyst was mixed with the spent catalyst that was used in the 1$^{st}$ recycling test (fresh catalyst:spent catalyst=2:8, weight ratio). In the same manner, 3$^{rd}$ recycling test was also examined.

Ethanol Dehydration Over P-SPP and ZSM-5 Catalysts

The ethanol dehydration reaction was carried out in a continuous flow fixed-bed quartz reactor of ½ in. O.D. coupled with a vertical heating jacket. Zeolite was placed in the middle of the reactor by a quartz frit. Prior to the reactions, the zeolite was activated at 550° C. under 30 mL/min air flow for 2 hrs. Thereafter, the reactor was cooled down to the reaction temperature with a constant He flow. Ethanol was introduced into the reactor by a liquid pump (Fisher, KDS100) with He as carrier flow. The gas line was heated to 80° C. to prevent condensation of ethanol. The reaction occurred at 1 atm for 10 min, and the products were collected using a 500 mL air bag (SKC, Tedlar). The products were identified using an Agilent 7890B GC coupled with FID detector.

What is claimed is:

1. A catalyst comprising:
   a porous material, wherein the porous material is a molecular sieve framework comprising:
   a zeolite beta (BEA) defining micropores bounded by 12-membered tetrahedral atom rings;
   silicon;
   aluminum; and
   phosphorus coupled to the porous material,
   wherein a ratio of silicon atoms to aluminum atoms in the molecular sieve framework is at least 1000:1; and
   wherein when 2,5-dimethylfuran and ethylene are contacted in the presence of the catalyst, and after dehydration, p-xylene is produced in a yield of at least 90%.

2. The catalyst of claim 1, wherein a ratio of silicon atoms to phosphorus atoms is in a range of 3:1 to 150:1.

3. A method of synthesizing the catalyst of claim 1, the method comprising:
   contacting a porous material with a phosphorus-containing compound to yield a wet porous material comprising phosphorus;
   removing water from the wet porous material comprising phosphorus to yield a dry porous material comprising phosphorus; and
   calcining the dry porous material comprising phosphorus to yield a catalyst comprising phosphorus coupled to the porous material.

4. The method of claim 3, further comprising solvothermally synthesizing the porous material in the presence of the phosphorus-containing compound to yield the wet porous material comprising phosphorus.

5. The method of claim 3, further comprising removing aluminum from the porous material before contacting the porous material with the phosphorus-containing compound.

6. The method of claim 3, wherein the phosphorus-containing compound comprises phosphoric acid.

7. The method of claim 3, wherein the phosphorus-containing compound comprises at least one of tetra(n-butyl) phosphonium hydroxide, tetramethyl phosphonium hydroxide, tetraethyl phosphonium hydroxide, and tetrapropyl phosphonium hydroxide.

8. A method for synthesizing p-xylene, the method comprising:
   contacting, in the presence of the catalyst of claim 1, biomass-derived 2,5-dimethylfuran with ethylene in a nonaqueous solvent to yield p-xylene.

9. The method of claim 8, wherein the contacting yields a cycloadduct, and further comprising catalyzing, with the catalyst, dehydration of the cycloadduct to yield the p-xylene.

10. The catalyst of claim 1, wherein a total pore volume of the porous material is about 0.8 cm$^3$/g.

11. The catalyst of claim 1, wherein a BET surface area obtained from argon adsorption-desorption isotherms is about 500 m$^2$/g.

* * * * *